(12) United States Patent
Lubberstedt et al.

(10) Patent No.: US 11,866,716 B2
(45) Date of Patent: Jan. 9, 2024

(54) METHODS AND COMPOSITIONS FOR GENERATING DOUBLED HAPLOID PLANTS AND USE OF SAME IN BREEDING

(71) Applicant: Iowa State University Research Foundation, Inc., Ames, IA (US)

(72) Inventors: Thomas Lubberstedt, Ames, IA (US); Ursula Karoline Frei, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 76 days.

(21) Appl. No.: 17/448,176

(22) Filed: Sep. 20, 2021

(65) Prior Publication Data

US 2022/0002739 A1 Jan. 6, 2022

Related U.S. Application Data

(62) Division of application No. 16/153,364, filed on Oct. 5, 2018, now Pat. No. 11,155,825.

(60) Provisional application No. 62/568,650, filed on Oct. 5, 2017.

(51) Int. Cl.
*C12N 15/82* (2006.01)
*C12N 9/12* (2006.01)
*A01H 1/08* (2006.01)

(52) U.S. Cl.
CPC .............. *C12N 15/82* (2013.01); *A01H 1/08* (2013.01); *C12N 9/12* (2013.01); *C12N 15/8213* (2013.01); *C12Y 207/11001* (2013.01)

(58) Field of Classification Search
CPC .................................. A01H 1/08; C12N 9/12
See application file for complete search history.

(56) References Cited

U.S. PATENT DOCUMENTS

| | | |
|---|---|---|
| 2003/0005479 A1 | 1/2003 | Kato |
| 2016/0057953 A1 | 3/2016 | Chan et al. |
| 2016/0212956 A1 | 7/2016 | Boutilier et al. |
| 2017/0022574 A1 | 1/2017 | Dhawan et al. |
| 2017/0067067 A1 | 3/2017 | Chintamanani et al. |

OTHER PUBLICATIONS

De La Fuente, Gerald N., Thesis (2015) Iowa State University, 153 pages; Improvement to the maize (*Zea mays* L.) in vivo maternal doubled haploid system. (Year: 2015).*
De La Fuente, G N. Thesis (2015) Iowa State University, 153 pages. (Year: 2015).*
Bowie et al., "Deciphering the message in protein sequences: tolerance to amino acid substitutions", Science, vol. 16, No. 247, pp. 1306-1310, 1990.
McConnell et al., "Role of PHABULOSA and PHAVOLUTA in determining radial patterning in shoots", Nature, vol. 411, (6838), pp. 709-713, 2001.
Kano-Murakami et al., "A rice homeotic gene, OSH1, causes unusual phenotypes in transgenic tobacco", FEBS Lett., vol. 334, No. 3, pp. 365-368, 1993.
Paganelli et al., "3 BUB1 and BUBR1/MAD3-related spindle assembly checkpoint proteins are required for accurate mitosis in *Arabidopsis*", New Phytologist, vol. 205, Issue 1, pp. 202-215, 2015.
Caillaud et al., "Spindle Assembly Checkpoint Protein Dynamics Reveal Conserved and Unsuspected Roles in Plant Cell Division", PLOS One, vol. 4, Issue 8, 9 pages, Aug. 2009.
De La Fuente, Gerald, "Improvements to the maize (*Zea mays* L.) in vivo maternal doubled haploid system", Iowa State University, Graduate Theses and Dissertations, 153 pages, 2015.
Kleiber et al., "Haploid Fertility in Temperate and Tropical Maize Germplasm", Crop Science, vol. 52, pp. 623-630, Mar. 2012.
Prasanna et al., "Doubled Haploid, Technology in Maize Breeding: Theory and Practice", International Maize and Wheat Improvement Center, 56 pages, 2012.
Ren et al., "QTL mapping for haploid male fertility by a segregation distortion method and fine mapping of a key QTL qhmf4 in maize", Theor Appl Genet, 11 pages, Apr. 7, 2017.

* cited by examiner

*Primary Examiner* — Russell Kallis
(74) *Attorney, Agent, or Firm* — McKee, Voorhees & Sease, PLC

(57) ABSTRACT

The present invention generally provides methods to generate plants with high frequency of spontaneous haploid genome doubling for use in doubled haploid production. The invention relates to the BUBR1 nucleic acid and protein sequences identified, which are associated with spontaneous haploid genome doubling.

8 Claims, 7 Drawing Sheets
Specification includes a Sequence Listing.

CLUSTAL O(1.2.4) multiple sequence alignment of genomic DNA

- Exons
- Non-translated 3' end
- DNA polymorphisms between GF1 and B73
- Region of MAD/BUB1 domain
- PCR primer

```
GF1_genomic-region_4221bp    CTTTAACAACCACTCTATATTTTGATCTATCTCTTTTATAAGTTTGAGTTCATGTGACTT    60
B73RefGen4_genomic-region    -------------------------gatctatctcttttataagtttgagttcatgtgactt    37
                                                      ******** ***************************

GF1_genomic-region_4221bp    ATTTTAGAAACTTGAGCTTACAAACTTTCTCTTATTTGGTCTCTGTATAGCGGAATTATG    120
B73RefGen4_genomic-region    attttagaaacttgagcttacaaactttctcttatttggtctctgtatataggaattatg    97
                             **************************************************  ********

GF1_genomic-region_4221bp    TCATTCTATAATCTATGTTCGTTCAGTCAGTCGTTATGAACTCTCTTATAGTCGCTCATT    180
B73RefGen4_genomic-region    tcattctataatctatgttcgttcagtcagtcgttatgaactctcttataatcgctcatt    157
                             ************************************************** *********

GF1_genomic-region_4221bp    TCATTGGTTGTGTTGTACCAAGACATATTGGATGGAGTAAACAATAACATCAGTTAGCCA    240
B73RefGen4_genomic-region    tcattggttgtgttgtaccaagacatactggatggagtaaacaataacatcagttagcca    217
                             **************************** *******************************

GF1_genomic-region_4221bp    AATCAAAATAACATTATACGGAGAGCAGAGACAAATAATAAAAAATCTTGATATTTTTTA    300
B73RefGen4_genomic-region    aatcaaaaaaacattatacggagagcagagacaaataataaaaaatcttgatatt-ttta    276
                             ********  *******************************************  ****

GF1_genomic-region_4221bp    TGGATTTACGTGGGTATTGTTGTAAGCCGTCGTAACGCACGGGTAACCGACTAGTATTAG    360
B73RefGen4_genomic-region    tggatttacgtgggtattgttgtaagccgtcgcaacgcacgggtaaccgactagtattag    336
                             ******************************** ***************************

GF1_genomic-region_4221bp    TAATAATTGAGTTATATCTATGAATTTTAAGCCTTCTCACGTTGAGCGCAACAAAATATT    420
B73RefGen4_genomic-region    taataattgagttatatctatgaattttaagcctcctcacgttgagcgcaacaaaatatt    396
                             **********************************  ************************

GF1_genomic-region_4221bp    TAATGAATAATTAGCCAACCTACTTATTCAAAATAATTACTATTGTATTGTATCATAAG    480
B73RefGen4_genomic-region    taatgaataattagccaacctacttattcaaaataattactattgtattgtatcataag    456
                             ************************************************************

GF1_genomic-region_4221bp    TAGTATTGTGCAAATTAAAGAATGATCCAAATTTTGTGTCGGGTGTGGGTCACCAATGGG    540
B73RefGen4_genomic-region    tagtattgtgcaaattaaagaatgatccaaattttgtgtcgggtgtgggtcacccatggt    516
                             ****************************************************** ****

GF1_genomic-region_4221bp    TTGAAGTAGAAACCTGCATAACACTCGTGAACTTTGAGTCGAGTGTGGGGTGCACTCACG    600
B73RefGen4_genomic-region    tgaaatagaaacctgcataacactcgtgaaactttgagtcgagtctggggtgcactcacg    576
                             * **  ** *   *             ***************** ***************

GF1_genomic-region_4221bp    GGTTAAAATTTTTACCTGTACCCGCACCCGTCGGGTTGGGTACGTGTCGAGTTTTGGGTT    660
B73RefGen4_genomic-region    ggttaaaattttacctgtacccgcacccgtcggggttgggtacgtgtcgagtttcgggtt    636
                             *********************************************************  *****

GF1_genomic-region_4221bp    TGCGGGTTAAATTGCCATCCCTACATAAAAGTGTAGAGGGGAGGAAAGACATGAGTGTGC    720
B73RefGen4_genomic-region    tgcgggttaaattgccatccctacataaaagtgtaggggggaggaaagacatgagtatgc    696
                             ************************************ **************** ** ***

GF1_genomic-region_4221bp    TCACATCCGATCGTTTTGATGAAGTAGAGACATCTCAATTATTTATGATATATTTTCATA    780
B73RefGen4_genomic-region    tcacatccgatcgttttgatggagcagagacatctcaattatttatgatatattttata    756
                             ********************* **  ******************************* *

GF1_genomic-region_4221bp    CGGAGACTATAGGAGTCGCTTTACTCTCTTTCATTAGAAACCAAACATCTAAAAAAATA    840
B73RefGen4_genomic-region    cggagactataagagtcgctttactctctttcattagaaaccaaacatctacaaaaaata    816
                             ***********  ************************************** ********

GF1_genomic-region_4221bp    GAACTGGATTGGTTCCATTCGCATCCACTCTTTTACCAAACACATCCTAATATATGTACT    900
B73RefGen4_genomic-region    gaactggattggttccattcgcatccactcttttaccaaacacatcctaatatatgtact    876
                             ************************************************************
```

FIG. 1A

```
GF1_genomic-region_4221bp    TGGTGGAGTAATTTAGTCCTCGTTTCATGGTTGCTTTT------TTTTGCTAAAATTTAC 954
B73RefGen4_genomic-region    tggtggagtaatttagtcctcgtttcatggttgcttttttttttttttttgctaaaatttac 936
                             ****************************************          ************

GF1_genomic-region_4221bp    GCTTCTCATGGCATACAGCCAGTTGAATTTGTTCCAGCCAAGCAAAACATAGCTGGGCTA 1014
B73RefGen4_genomic-region    gcttctcatggcatacagccagttgaatttgttccagccaagcaaaacatagctgggcta 996
                             ************************************************************

START
GF1_genomic-region_4221bp    TTTTGAGTACAAACCGGCCCAAATAAAAC████████████████████████████████ 1074
B73RefGen4_genomic-region    ttttgagtacaaaccggcccaaataaaac████████████████████████████████ 1056
                             ****************************   ************ *******************
                                                           M  G     T  K  S  L  R  P  K  L  11

GF1_genomic-region_4221bp    ████████████████████████████████████████████████████████████ 1134 EXON 1
B73RefGen4_genomic-region    ████████████████████████████████████████████████████████████ 1116
                             ************************************************************
                             F  A  K  L  H  R  L  K  P  K  P  D  L  R  A  A  A  A  S  A  31

GF1_genomic-region_4221bp    ████████████████████████████████████████████████████████████ 1194
B73RefGen4_genomic-region    ████████████████████████████████████████████████████████████ 1176
                             ************************************************************
                             P  K  R  N  G  R  I  S  S  N  S  N  C  S  R  C  H  P  P  H  51

GF1_genomic-region_4221bp    ████████████████████████████████████████████████████████████ 1254
B73RefGen4_genomic-region    ████████████████████████████████████████████████████████████ 1236
                             ************************************************************
                             M  A  A  A  E  E  M  M  A  V  L  Q  K  E  T  L  A  L  M  G  71

GF1_genomic-region_4221bp    ████████████████████████████████████████████████████████████ 1314
B73RefGen4_genomic-region    ████████████████████████████████████████████████████████████ 1296
                             ****************************   ****************************
                             L  G  N  A  A  A  A  V  V     E  C  E  K  F  K  E  N  A  R  91

GF1_genomic-region_4221bp    ████████████████████████████████████████████████████████████ 1374
B73RefGen4_genomic-region    ████████████████████████████████████████████████████████████ 1356
                             ************************************************************
                             P  L  K  R  G  R  D  V  S  K  L  N  H  A  L  K  A  H  A  D  111

GF1_genomic-region_4221bp    ██████████████████████████████████████GTACGTTTCCTTCTCCAGTCTTT 1434 INTRON 1-2
B73RefGen4_genomic-region    ██████████████████████████████████████gtacgtttccttctccagtcttt 1416
                             ************************************************************
                             P  A  Q  R  A  T  L  L  E  A  R  K                           123

GF1_genomic-region_4221bp    CGCCCAGCAATGGGGGAGAAAGAGTTGTGGTTTTGTAACTTTTGTTTGCTCTGGATTTCT 1494
B73RefGen4_genomic-region    cgcccagcaatggggga aaaggagttgtggttttgtaacttttgtttgctctggatttct 1476
                             ****************** ** *************************************

GF1_genomic-region_4221bp    TTTTCTTGGGCCTGGGTCTCTGGGGAGGAGACAAGTTGCTGCAGTAATGCAAATATATAT 1554
B73RefGen4_genomic-region    ttttcttgggcctgggtctgtggggaggagacaagttgctgcagtaatgcaaatatatat 1536
                             *******************  ***************************************

GF1_genomic-region_4221bp    CATGTGTGTTCATCGTTCGGTTCATTTGCTTGATCCAG████████████████████ 1614 Exon 2
B73RefGen4_genomic-region    catgtgtgttcatcgttcggttcatttgcttgatccag████████████████████ 1596
                             **************************************   ********************
                                                                    K  L  I  E  A  I  Y   130

GF1_genomic-region_4221bp    ████████████████████████████████████████GTAAGTTTTCTCGAAGCCCCT 1674 Intron 2-3
B73RefGen4_genomic-region    ████████████████████████████████████████gtaagttttctcatagccct 1656
                             ****************************************         ****  ******
                             E  Y  Q  G  E  D  P  L  Q  P  W  L  D                       143

GF1_genomic-region_4221bp    TTAACTCGCCTTTTTTCGATTTCTTGGTTCGTGCCAGGACTGGTAGCTGTTCTAGCAGAT 1734
B73RefGen4_genomic-region    ttaactcgcctt-tttcgatttcttggttcgtgccaggactggtagctgttctagcagat 1715
                             ************ ***********************************************
```

```
GF1_genomic-region_4221bp  TGGTTAGTTGTGCATTGGTTTTAATACTTGATTAATCCATGTGAATGTATGAAGTTTCTT 2693
B73RefGen4_genomic-region  tggttagttgtgcattggttttaatacttgattaatccatgtgaatgtatgaagtttctt 2671
                           ************************************************************

GF1_genomic-region_4221bp  ATATTCGATTTTTATTGTCAG[                                      ] 2753 Exon 5
B73RefGen4_genomic-region  atattcgattttttattgtcag[                                     ] 2731
                           ************************************************************
                                                 K A K P L E K L E A V Y R   257

GF1_genomic-region_4221bp  [                                      ]GTTTGCTATTTAAATTACA 2813 Intron 5-6
B73RefGen4_genomic-region  [                                      ]gtttgctattcaaattaca 2791
                           **************************************        *** *********
                              A F L R R S I K K R E Q E                            270

GF1_genomic-region_4221bp  GCAGTGTTTATTTATCTTGAAGCCAATACCTCAGTTGAATGACTTCTTTCTTTTCCTGTA 2873
B73RefGen4_genomic-region  gcagtgtttatttatcttgaagccaatacctcagttgaatgacttctttcttttcctgta 2851
                           ************************************************************

GF1_genomic-region_4221bp  G[                                                          ] 2933 Exon 6
B73RefGen4_genomic-region  g[                                                          ] 2911
                           ************************************************************
                             Q D D T V D D D L P K R S F G N N L K R                290

GF1_genomic-region_4221bp  [      ]AGTAAGCTTGTTCAGTTTTACTCTGATTTAGCATGAACTTCGAGTGGCTG 2993 Intron 6-7
B73RefGen4_genomic-region  [      ]agtaagcttgttcagttttactctgatttagcatgaacttcgagtggctg 2971
                           ************************************************************
                                D E N                                                293

GF1_genomic-region_4221bp  CAACCTAATACATATGCAAACATGGCAGGA[                            ] 3053 Exon 7
B73RefGen4_genomic-region  caacctaatacatatgcaaacatggcagga[                            ] 3031
                           ************************************************************
                                                          N Q Q A G N S H L G      304

GF1_genomic-region_4221bp  [          ]GTCAGTACCTGTATGATGTGACAGATGTAAAATATCCATC 3113 Intron 7-8
B73RefGen4_genomic-region  [          ]gtcagtacctgtatgatgtgacagatgtaaaatatccatc 3091
                           ************************************************************
                             P P R A L Q R                                          310

GF1_genomic-region_4221bp  TAAACCTGGAGTTTGTTTTTTCTCATCATGTCACTGATTATGCCTTTGCACACTTGCGGA 3173
B73RefGen4_genomic-region  taaacctggagttt-ttttcctcatcatgtcactgattatgcctttgcacacttgcgga 3150
                           ************** ***** ***************************************

GF1_genomic-region_4221bp  ATCGATGCTAACAG[                                            ] 3233 Exon 8
B73RefGen4_genomic-region  atcgatgctaacag[                                            ] 3210
                           ************************************************************
                                            P L S V Y K D E S P L P N Q G          325

GF1_genomic-region_4221bp  [                                                          ] 3293
B73RefGen4_genomic-region  [                                                          ] 3270
                           **********************************  ***********************
                             L D R V R S K E N N T S W R   L G T R A                345

!
GF1_genomic-region_4221bp  [                                          ]GTACGTTTG 3353 Intron 8-9
B73RefGen4_genomic-region  [                                          ]gtactttg  3330
                           ******************************************   **** ***
                             E R N K E N N M M P A K W T S H K                      362

GF1_genomic-region_4221bp  CCATGCCATTT[            ]ATGTGAGACTTGCACCGAGGACAACTATT 3413
B73RefGen4_genomic-region  ccatgccattt[            ]atgtgagacttgcaccgaggacaactatt 3390
                           ************************************************************
                                      913-1FW GF1_genomic-region_4221bp  CAGTAACGAACTTG------------------TTGTACAG[                  ] 3454 Exon 9
B73RefGen4_genomic-region  cagtaacgaacttgtggtaacactgcattgttgttgtacag[                  ] 3450
                           **************                  ********                
                                                                      I P Q K L G A 369
```

FIG. 1D

```
GF1_genomic-region_4221bp  ░░░░░░░░GTATGTTATTTAACATGCTAGTGTTACTCTTTTTT-TTTTGAGATTGTT 3573 Intron 9-10
B73RefGen4_genomic-region  ░░░░░░░░gtatgttatttaacatgctagtgttactcttttctttttgagattgtt 3569
                           ********  ****************************** * *****************
                             D   C   T  ▓                                                   392

GF1_genomic-region_4221bp  CAAAGTTACTACAAAAACATATATGTCTAAATAGACTCTT---TTTCCCTTTGGATTGCT 3630
B73RefGen4_genomic-region  caaagttactacaaaaacatatatgtctaaatagactcttttttttcccttTggattgct 3629
                           ****************************************   ** *************

GF1_genomic-region_4221bp  GTAG░░░░░░░░░░░░░░░░░░░░░░░░░░░░░░░░░░░░░░░░░░░░░░░░░░░░░░░ 3690 Exon 10
B73RefGen4_genomic-region  gtag░░░░░░░░░░░░░░░░░░░░░░░░░░░░░░░░░░░░░░░░░░░░░░░░░░░░░░░ 3689
                           ****  *****************************************************
                                 E  P  A  R  P  V  P  K  S  P  N  P  S  V  L  K  L  R  Q  411

GF1_genomic-region_4221bp  ░░░░░░░░░░░░░░░░░░░░░░░░░░░░GTAAGTACAGCATAGCTCTTGTAGCTTCGGGTATT 3750 Intron 10-11
B73RefGen4_genomic-region  ░░░░░░░░░░░░░░░░░░░░░░░░░░░░gtaagtacagcatagctcttgtagcttcgggtatt 3749
                           **********************************************************
                           T  T  S  K  S  L  K  K                                    419

GF1_genomic-region_4221bp  TGGGAAACTATTGTCAGCAGTTCCCTAACCTCTGCGGTCTTTTCTTTGGAGCAG░░░░░ 3810 Exon 11
B73RefGen4_genomic-region  tgggaaactattgtcagcagttccctaacctctgcggtcttttctttggagcag░░░░░ 3809
                           ********************************************************
                                                                                E  T  421
                                                                                STOP GF1_genomic-region_4221bp  ░░░░░░░░░░░░░░░░░░░░░░░░░░░░░░░░░░░░░░░░░░░░░░░░░░░░░░ 3870
B73RefGen4_genomic-region  ░░░░░░░░░░░░░░░░░░░░░░░░░░░░░░░░░░░░░░░░░░░░░░░░░░░░░░ 3869
                           E  L  L  K  E  N  P  L  R  N  F  P  L  S  R  L  R  STOP GF1_genomic-region_4221bp  ░░░░░░░░░░░░░░░░░░░░░░░░░░░░░░░░░░░░░░░░░░░░░░░░░░░░░░ 3930
B73RefGen4_genomic-region  ░░░░░░░░░░░░░░░░░░░░░░░░░░░░░░░░░░░░░░░░░░░░░░░░░░░░░░ 3929
                           ************************************************************

GF1_genomic-region_4221bp  ░░░░░░░░░░░░░░░░░░░░░░░░░░░░░░░░░░░░░░░░░░░░░░░░░░░░░░ 3990
B73RefGen4_genomic-region  ░░░░░░░░░░░░░░░░░░░░░░░░░░░░░░░░░░░░░░░░░░░░░░░░░░░░░░ 3987
                           **************  ********************************************

GF1_genomic-region_4221bp  ░░░░░░░░░░░░░░░░░░░░░░░░░░░░░░░░░░░░░░░░░░░░░░░░░░░░░░ 4050
B73RefGen4_genomic-region  ░░░░░░░░░░░░░░░░░░░░░░░░░░░░░░░░░░░░░░░░░░░░░░░░░░░░░░ 4047
                           ********  ******  ******  * ********************************

GF1_genomic-region_4221bp  ░░░░░░░░░░░░░░░░░░░░░░░░░░░░░░░░░░░░░░░░░░░░░░░░░░░░░░ 4110
B73RefGen4_genomic-region  ░░░░░░░░░░░░░░░░░░░░░░░░░░░░░░░░░░░░░░░░░░░░░░░░░░░░░░ 4104
                           ***  *********************************  *****  ***************

GF1_genomic-region_4221bp  ░░░░░░░░░░░░░░░░░░░░░░░░░░░░░░░░░░░░░░░░░░░░░░░░░░░░░░ 4170
B73RefGen4_genomic-region  ░░░░░░░░░░░░░░░░░░░░░░░░░░░░░░░░░░░░░░░░░░░░░░░░░░░░░░ 4164
                           ******************************  *******  *****************

GF1_genomic-region_4221bp  ░░░░░░░░░░░░░░░░░░░░░░GTGAATCCCGCGGCCATGGCGGCCGGAG---------- 4220
B73RefGen4_genomic-region  ░░░░░░░░░░░░░░░░░░░░░░ttatatttgaatgcctgagaaattagaaaacatatttg 4224
                           **********  ***  *   *   **    ***   *   **
```

FIG. 1E

CLUSTAL O(1.2.4) multiple sequence alignment

```
lcl|GRMZM2G009913_P01    MGLTKSLRPKLFAKLHRLKPKPDLRAAAASAPKRNGRISSNSNCSRCHPPHMAAAEEMMA 60
protein_of_SHGD_Allele   MGVTKSLRPKLFAKLHRLKPKPDLRAAAASAPKRNGRISSNSNCSRCHPPHMAAAEEMMA 60
                         :******************************************************* lcl|GRMZM2G009913_P01    VLDKETLALMGLGNAAAAVVECEKFKENARPLKRGRDVSKLNHALKAHADPAQRATLLE 120
protein_of_SHGD_Allele   VLDKETLALMGLGNAAAAVVECEKFKENARPLKRGRDVSKLNHALKAHADPAQRATLLE 120
                         *********************************************************** lcl|GRMZM2G009913_P01    ARKKLIEAIYEYQGEDPLQPWLDCIKWVQEYFPTGGECSGLVVLYEQCVRTLLDDERYKD 180
protein_of_SHGD_Allele   ARKKMIEAIYEYQGEDPLQPWLDCIKWVQEYFPTGGECSGLVVLYEQCVRTLLDDERYKD 180
                         **:***************************************************** lcl|GRMZM2G009913_P01    DLRFLKVWLEYAGNCADAEVIYRFLEANQIGQGHAIYYMSYASILESKNKLRKANEIIL 240
protein_of_SHGD_Allele   DLRFLKVWLEYAGNCADAEVIYRFLEANQIGQGHAIYYMSYASIMESKNKLRKANEIIL 240
                         *****************************************:************* lcl|GRMZM2G009913_P01    GIARKAKPLEKLEAVYRAFLRRSIKKREQEQDDTVDDDLPKRSFGNNLKRDENRNQQAGN 300
protein_of_SHGD_Allele   GIARKAKPLEKLEAVYRAFLRRSIKKREQEQDDTVDDDLPKRSFGNNLKRDENRNQQAGN 300
                         *********************************************************** lcl|GRMZM2G009913_P01    SHLGRPRALQRPLSVYKDESPLPNQGLDRVRSKENNTSWRLGTRAERNKENNMMPAKWT 360
protein_of_SHGD_Allele   SHLGRPRALQRPLSVYKDESPLPNQGLDRVRSKENNTSWRLGTRAERNKENNMMPAKWT 360
                         *********************************************************** lcl|GRMZM2G009913_P01    SHKIPQKLGARGAVQSTRASCSIEVFVEEDCTQEPARPVPKSPNPSVLKLRQTTSKSLKK 420
protein_of_SHGD_Allele   SHKIPQKLGARGAVQSTRASCSIEVFVEEDCTHEPARPVPKSPNPSVLKLRQTTSKSLKK 420
                         ******************************:************************ lcl|GRMZM2G009913_P01    ETELLKENPLRNFPLSRLR    439
protein_of_SHGD_Allele   ETELLKENPLRNFPLSRLR    439
                         *******************
```

A : (colon) indicates conservation between groups of strongly similar properties
A . (period) indicates conservation between groups of weakly similar properties as below

FIG. 2

Comparison of the MAD-BUB1 domain in GF1, B73, PH207, other Poaceae, and Arabidopsis

```
A.thaliana                    LIEKRRNLIEAIDEYEGDDPLSPWIECIKWVQEAFPPGGECSGLLVIYEQCVRKFWHSER 60
Sorghum                       LLETRKKMIEAIDQYQGEDPLQPWLDCIKWVQESFPTGGECSGLVVLYEQCVRTFWHDGR 60
Setaria                       LLEARRRMIEAIYEYQGEDPLQPWLDCIKWVQESFPTGGECSGLVVLYEQCVRTFWHDER 60
GF1/119-242                   LLEARKKMIEAIYEYQGEDPLQPWLDCIKWVQEYFPTGGECSGLVVLYEQCVRTLLDDER 60
B73/119-242                   LLEARKKLIEAIYEYQGEDPLQPWLDCIKWVQEYFPTGGECSGLVVLYEQCVRTLLDDER 60
PH207:Zm00008a021341_T001     LLEARKKLIEAIYEYQGEDPLQPWLDCIKWVQEYFPTGGECSGLVVLYEQCVRTLLDDER 60
Oryza                         LLAARRKMIEAIDEYSGEDPLQPWIDCIKWVQESFPTGGDCSGLVVIYEQCVRAFWHDDR 60
Brachypodium                  LLAERRRMIEAIEEYQGEDPLQPWVNCIKWVQESFPAGGESSGLVVIYEQCVRAFWHDER 60
Hordeum                       LLAERRRMIEAIDEYQGEDPLQPWVDCIKWVQESFPAGGEFSGLVVIYEQCVRAFWHDER 60
Triticum                      LLAERGRMIQAIEEYQGEDPLQPWVDCIKWVQESFPAGGEFSGLVVIYEQCVRAFWHDER 60
Aegilops                      LLAERRRMIEATEEYQGEDPLQPWVECIKWVQESFPAGGEFSGLVVIYEQCVRAFWHDER 60
                              *:   *  .:*:*   :*.*:***.**::*******  **  *.  ***:*:****** : .. *

A.thaliana                    YKDDLRYLKVWLEYA----EHCADAEVIYKFLEVNEIGKTHAVYYIAYALHIEFKNKVKT 116
Sorghum                       YKDDLRFLKVWLEYA-----GNCADAEVIYRFLEANQIGQGHAIYYMAYASLMESKNKLRK 116
Setaria                       YKDDLRFLKVWLEYA-----GNCADAEVIYKFLEANQIGQGHAIYYMSYASLLEAKNKLRK 116
GF1/119-242                   YKDDLRFLKVWLEYA-----GNCADAEVIYRFLEANQIGQGHAIYYMSYASLMESKNKLRK 116
B73/119-242                   YKDDLRFLKVWLEYA-----GNCADAEVIYRFLEANQIGQGHAIYYMSYASLLESKNKLRK 116
PH207:Zm00008a021341_T001     YKDDLRFLKVWLEYA-----GNCADAEVIYRFLEANQIGQGHAIYYMSYASLLESKNKLRK 116
Oryza                         YKNDLRYLKVWLEYA-----GNCADSEVIFRFLEANQIGQSHTNYYLSYASVMESKNKLKK 116
Brachypodium                  YKGDLRYLKVWLEYA-----GNCADAEVIFRFLEANQIGDGHAVFYIHYSSLMESKNKLKK 116
Hordeum                       YKDDLRYLKVWLEYA-----GNCSDAEVIFRFLESNQIGEGHAVFYIRYALLMESKNKLKK 116
Triticum                      YKDDLRYLKVWLEYFGLQAGNCSDAEVIFRFLESNQIGEGHAVFYIRYALLMESKNKLKK 120
Aegilops                      YKDDLRYLKVWLEYFGLQAGNCSDAEVIFRFLESNQIGEGHAVFYIRYASLMESKNKLKK 120
                              **.****:*******        :*:*:***:*** *:** . *: :*: *:   :* ***::.

A.thaliana                    ANEIFNLGI 125
Sorghum                       AKEIFDLGI 125
Setaria                       ANEIFDIGI 125
GF1/119-242                   ANEIF LGI 125
B73/119-242                   ANEIFDLGI 125
PH207:Zm00008a021341_T001     ANEIFDLGI 125
Oryza                         ANEIFNLGI 125
Brachypodium                  ANEIYNLGI 125
Hordeum                       ADEIF LGI 125
Triticum                      ADEIFNLGI 129
Aegilops                      ADEIFNLGI 129
                              *.**: :**
```

FIG. 3

SEQUENCE LISTING

```
<160> NUMBER OF SEQ ID NOS: 23

<210> SEQ ID NO 1
<211> LENGTH: 4220
<212> TYPE: DNA
<213> ORGANISM: Zea mays

<400> SEQUENCE: 1
ctttaacaac cactctatat tttgatctat ctcttttata agtttgagtt catgtgactt      60
attttagaaa cttgagctta caaactttct cttatttggt ctctgtatag cggaattatg     120
tcattctata atctatgttc gttcagtcag tcgttatgaa ctctcttata gtcgctcatt     180
tcattggttg tgttgtacca agacatattg gatggagtaa acaataacat cagttagcca     240
aatcaaaata acattatacg gagagcagag acaaataata aaaaatcttg atattttta     300 tggatttacg tgggtattgt tgtaagccgt cgtaacgcac gggtaaccga ctagtattag     360
taataattga gttatatcta tgaattttaa gccttctcac gttgagcgca acaaaatatt     420
taatgaataa ttagccaacc tacttattca aaaataatta ctattgtatt gtatcataag     480
tagtattgtg caaattaaag aatgatccaa attttgtgtc gggtgtgggt caccaatggg     540
ttgaagtaga aacctgcata acactcgtga aactttgagt cgagtgtggg gtgcactcac     600
gggttaaaat ttttacctgt acccgcaccc gtcgggttgg gtacgtgtcg agttttgggt     660
ttgcgggtta aattgccatc cctacataaa agtgtagagg ggaggaaaga catgagtgtg     720
ctcacatccg atcgtttga tgaagtagag acatctcaat tatttatgat atattttcat     780
acggagacta taggagtcgc tttactctct ttcattagaa accaaacatc taaaaaaaat     840
agaactggat tggttccatt cgcatccact cttttaccaa acacatccta atatatgtac     900
ttggtggagt aatttagtcc tcgtttcatg gttgcttttt tttgctaaaa tttacgcttc     960
tcatggcata cagccagttg aatttgttcc agccaagcaa aacatagctg ggctattttg    1020
```

```
agtacaaacc ggcccaaata aaacatggga gtaactaaaa gcctacggcc caaacttttc    1080
gcaaagcttc accgtttaaa accgaaacct gacctgcggg ctgcagcagc gtccgctcca    1140
aaacgcaacg gtcgaatctc ctcgaattcg aattgcagcc ggtgccaccc acctcacatg    1200
gcggcggcgg aagagatgat ggcggtgctg acaaggaga cgctggcgct gatgggtctg     1260
ggcaacgccg ccgccgcggt ggttgtcgag tgcgagaagt tcaaggagaa cgcgaggccg    1320
ctcaagcgcg ggcgcgacgt gtccaaactc aaccacgcgc tcaaggcaca cgccgatccc    1380
gcccagcgcg ccactcttct cgaagcccga agtacgtttt ccttctccag tctttcgccc    1440
agcaatgggg gagaaagagt tgtggttttg taacttttgt ttgctctgga tttctttttc    1500
ttgggcctgg gtctctgggg aggagacaag ttgctgcagt aatgcaaata tatatcatgt    1560
gtgttcatcg ttcggttcat ttgcttgatc caggaagatg attgaggcaa tctacgagta    1620
ccaaggcgag gatccgctcc aaccgtggct ggagtaagtt tttctcgaag cccctttaac    1680
tcgccttttt tcgatttctt ggttcgtgcc aggactggta gctgttctag cagatagatt    1740
gttcatttct tctctgattc gtccgcgtgc agctgcatca agtgggtgca ggagtatttt    1800
ccgaccggcg gcgagtgctc agggttggtg gtgttgtacg agcagtgcgt gcggaccta    1860 ttggatgacg agcgctacaa ggacgacctc cgcttcctca aagtgtggct ggaatacgtg    1920
agtgatgctt tgccagcttg attgttttc tctgtagttt gtgtcagtgc agtgaaggca    1980
cctcatatat cattccgctg ccgatcttgt cctttttgca ggcggggaac tgtgctgatg    2040
ctgaggtaat atacaggttc ctggaggcca accagattgg gcagggccat gcgatctact    2100
acatgtctta cgcatcgttg atggagtcaa gaacaagtt gaggaaagct aatgagatct     2160
ttgtccttgg tatagctagg tgagattttc tttagatcag cacgtttgtt catataaagc    2220
tcctgagttt taaattgttc ggtagatcat gctgttgtac tatatatccg atccaaaaat    2280
tgtgtcctat aatggacatg gagtgggtac atatatgctc ctgtgtttga ttttcgtaca    2340
taacaagagt caatgatggt acaaaaatga ggctgatgtt atactgaatc agttttcctt    2400
ctttgtttta tttccatgat cacttctaat ttgatacatg ctaacgaatt agaaatata    2460 agttcctttt agtttctagt ttgcaaacgt aaaatgaaaa aaaaatctta gtcttctact    2520
tcctattctt taagatttga cactcctttg actagttatg ccactatctt cttgtaaatg    2580
ataaacactc ggaattgttt tacttatcat ggtttctgct tacctctttt gttatggtta    2640
gttgtgcatt ggttttaata cttgattaat ccatgtgaat gtatgaagtt cttatattc     2700 gatttttat tgtcagaaaa gcgaagcctc tggagaagtt ggaagctgta tacagggcat     2760
ttcttcgaag atcaatcaaa aagagggaac aagaggtttg ctatttaaat tacagcagtg    2820
tttatttatc ttgaagccaa tacctcagtt gaatgacttc tttcttttcc gtagcagga     2880 tgatacagta gatgatgatc tgccaaaacg cagtttcggg aataacttga aacgagatga    2940
aaacagtaag cttgttcagt tttactctga tttagcatga acttcgagtg gctgcaacct    3000
aatacatatg caaacatggc aggaaatcag caagcaggga actcccacct ggggagacca    3060
agggcactgc agaggtcagt acctgtatga tgtgacagat gtaaaattc catctaaacc     3120 tggagtttgt tttttctcat caagtcactg attatgcctt tgcacacttg cggaatcgat    3180
gctaacaggc cgctttcagt ttacaaagat gaaagtccat taccaaatca gggccttgac    3240
agagtgagga gcaaagaaaa taacacaagt tggcgcaccc tcggaacacg agcagaacgg    3300
aacaaggaaa ataacatgat gcctgctaaa tggacgtctc acaaggtacg tttgccatgc    3360 cattttaggat tctctgaagt ggcccatgtg agacttgcac cgaggacaac tattcagtaa    3420
```

```
cgaacttgtt gtacagatcc cacagaagtt aggagcaaga ggagcggttc aatcaacccg    3480
agccagttgt tccattgaag tcttcgtcga ggaagactgc acacagtatg ttatttaaca    3540
tgctagtgtt actcttttt ttttgagatt gttcaaagtt actacaaaaa catatatgtc    3600
taaatagact ctttttccct ttggattgct gtagtgaacc tgctcggccg gtgccaaaga    3660
gcccaaatcc ttctgttctg aagctcaggc aaacaacaag caaaagcctt aagaagtaag    3720
tacagcatag ctcttgtagc ttcgggtatt tgggaaacta ttgtcagcag ttccctaacc    3780
tctgcggtct tttctttgga gcagggagac tgaattgctc aaggagaacc cgctgcgcaa    3840
cttccccctg agcaggctta ggtaatcagc atcttgctgg ttctgagaaa catctcgtac    3900
gttatgattt ggtcgtatgt atggttgctg tgaggtgttg tgcccaaaaa aaaggcttta    3960
ttagcctcta aagcttagac gagcaatgta tgcctatggc attacccaag tgctgtaagg    4020
ttctgcatta tattgacacg gcgtgcttat tattgataga cctgcagatc tcgtgcgtgc    4080
ctatgtgtat ctaatagcct cgcaaaataa tctgcttctg caaattctaa tagcttgttc    4140
tgtaatgaaa atgcctttgg actaatatct aatagcgtct cgttccttgc atgtgaatcc    4200
cgcggccatg gcggccggag                                              4220

<210> SEQ ID NO 2
<211> LENGTH: 4289
<212> TYPE: DNA
<213> ORGANISM: Zea mays

<400> SEQUENCE: 2
gatctatctt ttttataagt ttgagttcat gtgacttatt ttagaaactt gagcttacaa      60
actttctctt atttggtctc tgtatatagg aattatgtca ttctataatc tatgttcgtt     120
cagtcagtcg ttatgaactc tcttataatc gctcatttca ttggttgtgt tgtaccaaga     180
catactggat ggagtaaaca ataacatcag ttagccaaat caaaaaaaca ttatacggag     240
agcagagaca ataataaaaa atcttgata tttttatgga tttacgtggg tattgttgta     300
agccgtcgca acgcacgggt aaccgactag tattagtaat aattgagtta tatctatgaa     360
ttttaagcct tctcacgttg agcgcaacaa aatatttaat gaataattag ccaacctact     420
tattcaaaaa taattactat tgtattgtat cataagtagt attgtgcaaa ttaaagaatg     480
atccaaattt tgtgtcgggt gtgggtcacc catggttgaa atagaaacct gcataacact     540
cgtgaaactt tgagtcgagt ctggggtgca ctcacgggtt aaaattttta cctgtacccg     600
cacccgtcgg gttgggtacg tgtcgagttt cgggtttgcg ggttaaattg ccatccctac     660
ataaaagtgt agggggggagg aaagacatga gtatgctcac atccgatcgt tttgatggag     720
cagagacatc tcaattattt atgatatatt tttatacgga gactaaaga gtcgctttac     780 tctctttcat tagaaaccaa acatctacaa aaaatagaac tggattggtt ccattcgcat     840
ccactctttt accaaacaca tcctaatata tgtacttggt ggagtaattt agtcctcgtt     900
tcatggttgc tttttttttt ttttgctaaa atttacgctt ctcatggcat acagccagtt     960
gaatttgttc cagccaagca aaacatagct gggctatttt gagtacaaac cggcccaaat    1020
aaaacatggg attaactaaa agcctacggc ccaaacttt cgcaaagctt caccgtttaa    1080
aaccgaaacc tgacctgcgg gctgcagcag cgtccgctcc aaaacgcaac ggtcgaatct    1140
cctcgaattc gaattgcagc cggtgccacc cacctcacat ggcggcggcg aagagatga    1200 tggcggtgct ggacaaggag acgctggcgc tgatgggtct gggcaacgcc gccgccgcgg    1260
```

```
tggttgccga gtgcgagaag ttcaaggaga acgcgaggcc gctcaagcgc gggcgcgacg    1320
tgtccaaact caaccacgcg ctcaaggcac acgccgatcc cgcccagcgc gccactcttc    1380
tcgaagcccg aaagtacgtt tccttctcca gtctttcgcc cagcaatggg ggaaaaggag    1440
ttgtggtttt gtaactttg tttgctctgg atttcttttt cttgggcctg gtctgtggg     1500 gaggagacaa gttgctgcag taatgcaaat atatatcatg tgtgttcatc gttcggttca    1560
tttgcttgat ccaggaagct gattgaggca atctacgagt accaaggcga ggatccgctc    1620
caaccgtggc tggagtaagt ttttctcata gcccctttaa ctcgcctttt tcgatttctt    1680
ggttcgtgcc aggactggta gctgttctag cagatagatt gttcatttct tctctgattc    1740
gtccgcgtgc agctgcatca agtgggtgca ggagtatttt ccgaccggcg gcgagtgctc    1800
agggttggtg gtgttgtacg agcagtgcgt gcggacctta ttggacgacg agcgctacaa    1860
ggacgacctc cgcttcctca agtgtggct ggaatacgtg agtgatgctt tgccagcttg      1920 attgttttc tctgtagttt gtgtcagtgc agtggaggca cctcatatat cattccgctg      1980
ccgatcttgt cctttttgca ggcggggaac tgtgctgatg ctgaggtaat atacaggttc     2040
ctggaggcca accagattgg gcagggccat gcgatctact acatgtctta cgcatcgttg     2100
ctggagtcaa agaacaagtt gaggaaagct aatgagatct tgaccttgg tatagctagg      2160 tgagattttc tttagatcag cacgtttgtt catataaagc tcctgagttt taaattgtta     2220
ggtagatcat gctgttgtac tatatatccg atccaaaaat tgtgtcctat aatggacatg    2280
gagtacatat atgctcctgt gtttgatttt cgtacataac aagagtcaat gatggtacaa    2340
aaatgaggct gatgttatac tgaatcagtt ttccttctt gttttatttt catgatcact      2400
tctaatttga tacattctaa cgaattagaa ataaaagtt cctttagtt tctagttcgc       2460 aaacgtaaaa tgaaaaaaaa atctcagtct tctacttcct attctttaag atttgacact     2520
cctttgacta gttatgccac tatcttcttg taaatgatac aacactcgga attgttttac    2580
ttatcatggt ttctgcttac ctcttttgtt atggttagtt gtgcattggt tttaatactt    2640
gattaatcca tgtgaatgta tgaagtttct tatattcgat tttttattgt cagaaaagcg    2700
aagcctctgg agaagttgga agctgtatac agggcatttc ttcgaagatc aatcaaaaag    2760
agggaacaag aggtttgcta ttcaaattac agcagtgttt atttatcttg aagccaatac    2820
ctcagttgaa tgacttcttt cttttcctgt agcaggatga tacagtagat gatgatctgc    2880
caaaacgcag tttcgggaat aacttgaaac gagatgaaaa cagtaagctt gttcagtttt    2940
actctgattt agcatgaact tcgagtggct gcaacctaat acatatgcaa acatggcagg    3000
aaatcagcaa gcagggaact cccacctggg gagaccaagg gcactgcaga ggtcagtacc    3060
tgtatgatgt gacagatgta aaatatccat ctaaacctgg agttttttt cctcatcatg     3120 tcactgatta tgcctttgca cacttgcgga atcgatgcta acaggccgct ttcagtttac    3180
aaagatgaaa gtccattacc aaatcagggc cttgacagag tgaggagcaa agaaaataac    3240
acaagttggc gcgtcctcgg aacacgagca gaacggaaca aggaaaataa catgatgcct    3300
gctaaatgga cgtctcacaa ggtacttttg ccatgccatt taggattctc tgaagtggcc    3360
catgtgagac ttgcaccgag gacaactatt cagtaacgaa cttgtggtaa cactgcattg    3420
ttgttgtaca gattccacag aagttaggag caagaggagc ggttcaatca acccgagcca    3480
gttgttccat tgaagtcttc gtcgaggaag actgcacaca gtatgttatt aacatgcta    3540 gtgttactct tttcttttt gagattgttc aaagttacta caaaaacata tatgtctaaa    3600
tagactcttt ttttcccctt tggattgctg tagggaacct gctcggccgg tgccaaagag    3660
```

```
cccaaatcct tctgttctga agctcaggca acaacaagc aaaagcctta agaagtaagt   3720
acagcatagc tcttgtagct tcgggtattt gggaaactat tgtcagcagt tccctaacct   3780
ctgcggtctt ttctttggag cagggagact gaattgctca aggagaaccc gctgcgcaac   3840 ttcccctga gcaggcttag gtaatcagca tcttgctggt tctgagaaac atctcgtacg    3900
ttatgatttg gtcgtatgta tggttgctgt gaggtgttgt gcccaaaaaa ggctttatta   3960
gcctctaaag cttagacgag caatgtatgc ctatggcatt atccaagtga tgtaaggctg   4020
tgcattatat tgacacggcg tgcttattat gaatagacct gcagatctcg tgcgtgccta   4080
tgtgaatcta gcctcgcaaa ataatctgct tctgcaaatt ctaatagctt gttctgtaac   4140
gaaaatgcct ttggactaat atctaatagc gtctcattca gtttgtttat atttgaatgc   4200
ctgagaaatt agaaaacata tttgaatgtt ttattccgtc cataaatata gaatctctgt   4260
aagcatgtag ctaaactcaa tagaaacat                                    4289

<210> SEQ ID NO 3
<211> LENGTH: 439
<212> TYPE: PRT
<213> ORGANISM: Zea mays

<400> SEQUENCE: 3

Met Gly Val Thr Lys Ser Leu Arg Pro Lys Leu Phe Ala Lys Leu His
1               5                   10                  15

Arg Leu Lys Pro Lys Pro Asp Leu Arg Ala Ala Ala Ser Ala Pro
            20                  25                  30

Lys Arg Asn Gly Arg Ile Ser Ser Asn Ser Asn Cys Ser Arg Cys His
        35                  40                  45

Pro Pro His Met Ala Ala Ala Glu Glu Met Met Ala Val Leu Asp Lys
    50                  55                  60

Glu Thr Leu Ala Leu Met Gly Leu Gly Asn Ala Ala Ala Ala Val Val
65                  70                  75                  80

Val Glu Cys Glu Lys Phe Lys Glu Asn Ala Arg Pro Leu Lys Arg Gly
                85                  90                  95

Arg Asp Val Ser Lys Leu Asn His Ala Leu Lys Ala His Ala Asp Pro
            100                 105                 110

Ala Gln Arg Ala Thr Leu Leu Glu Ala Arg Lys Lys Met Ile Glu Ala
        115                 120                 125

Ile Tyr Glu Tyr Gln Gly Glu Asp Pro Leu Gln Pro Trp Leu Asp Cys
    130                 135                 140

Ile Lys Trp Val Gln Glu Tyr Phe Pro Thr Gly Glu Cys Ser Gly
145                 150                 155                 160

Leu Val Val Leu Tyr Glu Gln Cys Val Arg Thr Leu Leu Asp Asp Glu
                165                 170                 175

Arg Tyr Lys Asp Asp Leu Arg Phe Leu Lys Val Trp Leu Glu Tyr Ala
            180                 185                 190

Gly Asn Cys Ala Asp Ala Glu Val Ile Tyr Arg Phe Leu Glu Ala Asn
        195                 200                 205

Gln Ile Gly Gln Gly His Ala Ile Tyr Tyr Met Ser Tyr Ala Ser Leu
    210                 215                 220

Met Glu Ser Lys Asn Lys Leu Arg Lys Ala Asn Glu Ile Phe Val Leu
225                 230                 235                 240

Gly Ile Ala Arg Lys Ala Lys Pro Leu Glu Lys Leu Glu Ala Val Tyr
                245                 250                 255
```

```
Arg Ala Phe Leu Arg Arg Ser Ile Lys Lys Arg Glu Gln Glu Gln Asp
            260                 265                 270

Asp Thr Val Asp Asp Leu Pro Lys Arg Ser Phe Gly Asn Asn Leu
        275                 280                 285

Lys Arg Asp Glu Asn Arg Asn Gln Gln Ala Gly Asn Ser His Leu Gly
        290                 295                 300

Arg Pro Arg Ala Leu Gln Arg Pro Leu Ser Val Tyr Lys Asp Glu Ser
305                 310                 315                 320

Pro Leu Pro Asn Gln Gly Leu Asp Arg Val Arg Ser Lys Glu Asn Asn
                    325                 330                 335

Thr Ser Trp Arg Thr Leu Gly Thr Arg Ala Glu Arg Asn Lys Glu Asn
            340                 345                 350

Asn Met Met Pro Ala Lys Trp Thr Ser His Lys Ile Pro Gln Lys Leu
            355                 360                 365

Gly Ala Arg Gly Ala Val Gln Ser Thr Arg Ala Ser Cys Ser Ile Glu
            370                 375                 380

Val Phe Val Glu Glu Asp Cys Thr His Glu Pro Ala Arg Pro Val Pro
385                 390                 395                 400

Lys Ser Pro Asn Pro Ser Val Leu Lys Leu Arg Gln Thr Thr Ser Lys
                    405                 410                 415

Ser Leu Lys Lys Glu Thr Glu Leu Leu Lys Glu Asn Pro Leu Arg Asn
            420                 425                 430

Phe Pro Leu Ser Arg Leu Arg
            435

<210> SEQ ID NO 4
<211> LENGTH: 439
<212> TYPE: PRT
<213> ORGANISM: Zea mays

<400> SEQUENCE: 4

Met Gly Leu Thr Lys Ser Leu Arg Pro Lys Leu Phe Ala Lys Leu His
1               5                   10                  15

Arg Leu Lys Pro Lys Pro Asp Leu Arg Ala Ala Ala Ser Ala Pro
            20                  25                  30

Lys Arg Asn Gly Arg Ile Ser Ser Asn Ser Asn Cys Ser Arg Cys His
            35                  40                  45

Pro Pro His Met Ala Ala Ala Glu Glu Met Met Ala Val Leu Asp Lys
            50                  55                  60

Glu Thr Leu Ala Leu Met Gly Leu Gly Asn Ala Ala Ala Val Val
65                  70                  75                  80

Ala Glu Cys Glu Lys Phe Lys Glu Asn Ala Arg Pro Leu Lys Arg Gly
                85                  90                  95

Arg Asp Val Ser Lys Leu Asn His Ala Leu Lys Ala His Ala Asp Pro
            100                 105                 110

Ala Gln Arg Ala Thr Leu Leu Glu Ala Arg Lys Lys Leu Ile Glu Ala
            115                 120                 125

Ile Tyr Glu Tyr Gln Gly Glu Asp Pro Leu Gln Pro Trp Leu Asp Cys
            130                 135                 140

Ile Lys Trp Val Gln Glu Tyr Phe Pro Thr Gly Gly Glu Cys Ser Gly
145                 150                 155                 160

Leu Val Val Leu Tyr Glu Gln Cys Val Arg Thr Leu Leu Asp Asp Glu
                165                 170                 175

Arg Tyr Lys Asp Asp Leu Arg Phe Leu Lys Val Trp Leu Glu Tyr Ala
            180                 185                 190
```

```
Gly Asn Cys Ala Asp Ala Glu Val Ile Tyr Arg Phe Leu Glu Ala Asn
            195                 200                 205

Gln Ile Gly Gln Gly His Ala Ile Tyr Tyr Met Ser Tyr Ala Ser Leu
    210                 215                 220

Leu Glu Ser Lys Asn Lys Leu Arg Lys Ala Asn Glu Ile Phe Asp Leu
225                 230                 235                 240

Gly Ile Ala Arg Lys Ala Lys Pro Leu Glu Lys Leu Glu Ala Val Tyr
                245                 250                 255

Arg Ala Phe Leu Arg Arg Ser Ile Lys Lys Arg Glu Gln Glu Gln Asp
            260                 265                 270

Asp Thr Val Asp Asp Leu Pro Lys Arg Ser Phe Gly Asn Asn Leu
    275                 280                 285

Lys Arg Asp Glu Asn Arg Asn Gln Gln Ala Gly Asn Ser His Leu Gly
290                 295                 300

Arg Pro Arg Ala Leu Gln Arg Pro Leu Ser Val Tyr Lys Asp Glu Ser
305                 310                 315                 320

Pro Leu Pro Asn Gln Gly Leu Asp Arg Val Arg Ser Lys Glu Asn Asn
                325                 330                 335

Thr Ser Trp Arg Val Leu Gly Thr Arg Ala Glu Arg Asn Lys Glu Asn
            340                 345                 350

Asn Met Met Pro Ala Lys Trp Thr Ser His Lys Ile Pro Gln Lys Leu
        355                 360                 365

Gly Ala Arg Gly Ala Val Gln Ser Thr Arg Ala Ser Cys Ser Ile Glu
    370                 375                 380

Val Phe Val Glu Glu Asp Cys Thr Gln Glu Pro Ala Arg Pro Val Pro
385                 390                 395                 400

Lys Ser Pro Asn Pro Ser Val Leu Lys Leu Arg Gln Thr Thr Ser Lys
                405                 410                 415

Ser Leu Lys Lys Glu Thr Glu Leu Leu Lys Glu Asn Pro Leu Arg Asn
            420                 425                 430

Phe Pro Leu Ser Arg Leu Arg
        435

<210> SEQ ID NO 5
<211> LENGTH: 1320
<212> TYPE: DNA
<213> ORGANISM: Zea mays

<400> SEQUENCE: 5
atgggagtaa ctaaaagcct acggcccaaa cttttcgcaa agcttcaccg tttaaaaccg      60
aaacctgacc tgcgggctgc agcagcgtcc gctccaaaac gcaacggtcg aatctcctcg     120
aattcgaatt gcagccggtg ccacccacct cacatggcgg cggcggaaga gatgatggcg     180
gtgctggaca aggagacgct ggcgctgatg gtctgggca  acgccgccgc cgcggtggtt     240
gtcgagtgcg agaagttcaa ggagaacgcg aggccgctca gcgcgggcg  cgacgtgtcc     300 aaactcaacc acgcgctcaa ggcacacgcc gatcccgccc agcgcgccac tcttctcgaa     360
gcccgaaaga gatgattga  ggcaatctac gagtaccaag gcgaggatcc gctccaaccg     420
tggctggact gcatcaagtg ggtgcaggag tattttccga ccggcggcga gtgctcaggg     480
ttggtggtgt tgtacgagca gtgcgtgcgg accttattgg atgacgagcg ctacaaggac     540
gacctccgct tcctcaaagt gtggctgaa  tacgcgggga actgtgctga tgctgaggta     600
atatacaggt tcctggaggc caaccagatt gggcagggcc atgcgatcta ctacatgtct     660
```

| tacgcatcgt tgatggagtc aaagaacaag ttgaggaaag ctaatgagat ctttgtcctt | 720 |
| ggtatagcta gaaaagcgaa gcctctggag aagttggaag ctgtatacag ggcatttctt | 780 |
| cgaagatcaa tcaaaaagag ggaacaagag caggatgata cagtagatga tgatctgcca | 840 |
| aaacgcagtt tcgggaataa cttgaaacga gatgaaaaca gaaatcagca agcagggaac | 900 |
| tcccacctgg ggagaccaag ggcactgcag aggccgcttt cagtttacaa agatgaaagt | 960 |
| ccattaccaa atcagggcct tgacagagtg aggagcaaaa aaataacac aagttggcgc | 1020 |
| accctcggaa cacgagcaga acggaacaag gaaaataaca tgatgcctgc taaatggacg | 1080 |
| tctcacaaga tcccacagaa gttaggagca agaggagcgg ttcaatcaac ccgagccagt | 1140 |
| tgttccattg aagtcttcgt cgaggaagac tgcacacatg aacctgctcg gccggtgcca | 1200 |
| aagagcccaa atccttctgt tctgaagctc aggcaaacaa caagcaaaag ccttaagaag | 1260 |
| gagactgaat tgctcaagga gaacccgctg cgcaacttcc ccctgagcag gcttaggtaa | 1320 |

<210> SEQ ID NO 6
<211> LENGTH: 1320
<212> TYPE: DNA
<213> ORGANISM: Zea mays

<400> SEQUENCE: 6

| atgggattaa ctaaaagcct acggcccaaa cttttcgcaa agcttcaccg tttaaaaccg | 60 |
| aaacctgacc tgcgggctgc agcagcgtcc gctccaaaac gcaacggtcg aatctcctcg | 120 |
| aattcgaatt gcagccggtg ccacccacct cacatggcgg cggcggaaga gatgatggcg | 180 |
| gtgctggaca aggagacgct ggcgctgatg ggtctgggca acgccgccgc cgcggtggtt | 240 |
| gccgagtgcg agaagttcaa ggagaacgcg aggccgctca gcgcgggcg cgacgtgtcc | 300 |
| aaactcaacc acgcgctcaa ggcacacgcc gatcccgccc agcgcgccac tcttctcgaa | 360 |
| gcccgaaaga agctgattga ggcaatctac gagtaccaag gcgaggatcc gctccaaccg | 420 |
| tggctggact gcatcaagtg ggtgcaggag tattttccga ccggcggcga gtgctcaggg | 480 |
| ttggtggtgt tgtacgagca gtgcgtgcgg accttattgg acgacgagcg ctacaaggac | 540 |
| gacctccgct tcctcaaagt gtggctgaa tacgcgggga actgtgctga tgctgaggta | 600 |
| atatacaggt tcctggaggc caaccagatt gggcagggcc atgcgatcta ctacatgtct | 660 |
| tacgcatcgt tgctggagtc aaagaacaag ttgaggaaag ctaatgagat ctttgacctt | 720 |
| ggtatagcta gaaaagcgaa gcctctggag aagttggaag ctgtatacag ggcatttctt | 780 |
| cgaagatcaa tcaaaaagag ggaacaagag caggatgata cagtagatga tgatctgcca | 840 |
| aaacgcagtt tcgggaataa cttgaaacga gatgaaaaca gaaatcagca agcagggaac | 900 |
| tcccacctgg ggagaccaag ggcactgcag aggccgcttt cagtttacaa agatgaaagt | 960 |
| ccattaccaa atcagggcct tgacagagtg aggagcaaaa aaataacac aagttggcgc | 1020 |
| gtcctcggaa cacgagcaga acggaacaag gaaaataaca tgatgcctgc taaatggacg | 1080 |
| tctcacaaga ttccacagaa gttaggagca agaggagcgg ttcaatcaac ccgagccagt | 1140 |
| tgttccattg aagtcttcgt cgaggaagac tgcacacagg aacctgctcg gccggtgcca | 1200 |
| aagagcccaa atccttctgt tctgaagctc aggcaaacaa caagcaaaag ccttaagaag | 1260 |
| gagactgaat tgctcaagga gaacccgctg cgcaacttcc ccctgagcag gcttaggtaa | 1320 |

<210> SEQ ID NO 7
<211> LENGTH: 125
<212> TYPE: PRT
<213> ORGANISM: Arabidopsis thaliana

<400> SEQUENCE: 7

```
Leu Ile Glu Lys Arg Arg Asn Leu Ile Glu Ala Ile Asp Glu Tyr Glu
1               5                   10                  15
Gly Asp Asp Pro Leu Ser Pro Trp Ile Glu Cys Ile Lys Trp Val Gln
            20                  25                  30
Glu Ala Phe Pro Pro Gly Gly Glu Cys Ser Gly Leu Leu Val Ile Tyr
        35                  40                  45
Glu Gln Cys Val Arg Lys Phe Trp His Ser Glu Arg Tyr Lys Asp Asp
    50                  55                  60
Leu Arg Tyr Leu Lys Val Trp Leu Glu Tyr Ala Glu His Cys Ala Asp
65                  70                  75                  80
Ala Glu Val Ile Tyr Lys Phe Leu Glu Val Asn Glu Ile Gly Lys Thr
                85                  90                  95
His Ala Val Tyr Tyr Ile Ala Tyr Ala Leu His Ile Glu Phe Lys Asn
            100                 105                 110
Lys Val Lys Thr Ala Asn Glu Ile Phe Asn Leu Gly Ile
        115                 120                 125
```

<210> SEQ ID NO 8
<211> LENGTH: 125
<212> TYPE: PRT
<213> ORGANISM: Sorghum bicolor

<400> SEQUENCE: 8

```
Leu Leu Glu Thr Arg Lys Lys Met Ile Glu Ala Ile Asp Gln Tyr Gln
1               5                   10                  15
Gly Glu Asp Pro Leu Gln Pro Trp Leu Asp Cys Ile Lys Trp Val Gln
            20                  25                  30
Glu Ser Phe Pro Thr Gly Gly Glu Cys Ser Gly Leu Val Val Leu Tyr
        35                  40                  45
Glu Gln Cys Val Arg Thr Phe Trp His Asp Gly Arg Tyr Lys Asp Asp
    50                  55                  60
Leu Arg Phe Leu Lys Val Trp Leu Glu Tyr Ala Gly Asn Cys Ala Asp
65                  70                  75                  80
Ala Glu Val Ile Tyr Arg Phe Leu Glu Ala Asn Gln Ile Gly Gln Gly
                85                  90                  95
His Ala Ile Tyr Tyr Met Ala Tyr Ala Ser Leu Met Glu Ser Lys Asn
            100                 105                 110
Lys Leu Arg Lys Ala Lys Glu Ile Phe Asp Leu Gly Ile
        115                 120                 125
```

<210> SEQ ID NO 9
<211> LENGTH: 125
<212> TYPE: PRT
<213> ORGANISM: Setaria viridis

<400> SEQUENCE: 9

```
Leu Leu Glu Ala Arg Arg Arg Met Ile Glu Ala Ile Tyr Glu Tyr Gln
1               5                   10                  15
Gly Glu Asp Pro Leu Gln Pro Trp Leu Asp Cys Ile Lys Trp Val Gln
            20                  25                  30
Glu Ser Phe Pro Thr Gly Gly Glu Cys Ser Gly Leu Val Val Leu Tyr
        35                  40                  45
Glu Gln Cys Val Arg Thr Phe Trp His Asp Glu Arg Tyr Lys Asp Asp
    50                  55                  60
```

```
Leu Arg Phe Leu Lys Val Trp Leu Glu Tyr Ala Gly Asn Cys Ala Asp
 65                  70                  75                  80

Ala Glu Val Ile Tyr Lys Phe Leu Glu Ala Asn Gln Ile Gly Gln Gly
                 85                  90                  95

His Ala Ile Tyr Tyr Met Ser Tyr Ala Ser Leu Leu Glu Ala Lys Asn
            100                 105                 110

Lys Leu Arg Lys Ala Asn Glu Ile Phe Asp Ile Gly Ile
        115                 120                 125
```

<210> SEQ ID NO 10
<211> LENGTH: 125
<212> TYPE: PRT
<213> ORGANISM: Zea mays

<400> SEQUENCE: 10

```
Leu Leu Glu Ala Arg Lys Lys Met Ile Glu Ala Ile Tyr Glu Tyr Gln
 1               5                  10                  15

Gly Glu Asp Pro Leu Gln Pro Trp Leu Asp Cys Ile Lys Trp Val Gln
                 20                  25                  30

Glu Tyr Phe Pro Thr Gly Gly Glu Cys Ser Gly Leu Val Val Leu Tyr
             35                  40                  45

Glu Gln Cys Val Arg Thr Leu Leu Asp Asp Glu Arg Tyr Lys Asp Asp
         50                  55                  60

Leu Arg Phe Leu Lys Val Trp Leu Glu Tyr Ala Gly Asn Cys Ala Asp
 65                  70                  75                  80

Ala Glu Val Ile Tyr Arg Phe Leu Glu Ala Asn Gln Ile Gly Gln Gly
                 85                  90                  95

His Ala Ile Tyr Tyr Met Ser Tyr Ala Ser Leu Met Glu Ser Lys Asn
            100                 105                 110

Lys Leu Arg Lys Ala Asn Glu Ile Phe Val Leu Gly Ile
        115                 120                 125
```

<210> SEQ ID NO 11
<211> LENGTH: 125
<212> TYPE: PRT
<213> ORGANISM: Zea mays

<400> SEQUENCE: 11

```
Leu Leu Glu Ala Arg Lys Lys Leu Ile Glu Ala Ile Tyr Glu Tyr Gln
 1               5                  10                  15

Gly Glu Asp Pro Leu Gln Pro Trp Leu Asp Cys Ile Lys Trp Val Gln
                 20                  25                  30

Glu Tyr Phe Pro Thr Gly Gly Glu Cys Ser Gly Leu Val Val Leu Tyr
             35                  40                  45

Glu Gln Cys Val Arg Thr Leu Leu Asp Asp Glu Arg Tyr Lys Asp Asp
         50                  55                  60

Leu Arg Phe Leu Lys Val Trp Leu Glu Tyr Ala Gly Asn Cys Ala Asp
 65                  70                  75                  80

Ala Glu Val Ile Tyr Arg Phe Leu Glu Ala Asn Gln Ile Gly Gln Gly
                 85                  90                  95

His Ala Ile Tyr Tyr Met Ser Tyr Ala Ser Leu Leu Glu Ser Lys Asn
            100                 105                 110

Lys Leu Arg Lys Ala Asn Glu Ile Phe Asp Leu Gly Ile
        115                 120                 125
```

<210> SEQ ID NO 12
<211> LENGTH: 125

```
<212> TYPE: PRT
<213> ORGANISM: Zea mays

<400> SEQUENCE: 12

Leu Leu Glu Ala Arg Lys Lys Leu Ile Glu Ala Ile Tyr Glu Tyr Gln
1               5                   10                  15

Gly Glu Asp Pro Leu Gln Pro Trp Leu Asp Cys Ile Lys Trp Val Gln
                20                  25                  30

Glu Tyr Phe Pro Thr Gly Gly Glu Cys Ser Gly Leu Val Val Leu Tyr
            35                  40                  45

Glu Gln Cys Val Arg Thr Leu Leu Asp Asp Glu Arg Tyr Lys Asp Asp
        50                  55                  60

Leu Arg Phe Leu Lys Val Trp Leu Glu Tyr Ala Gly Asn Cys Ala Asp
65                  70                  75                  80

Ala Glu Val Ile Tyr Arg Phe Leu Glu Ala Asn Gln Ile Gly Gln Gly
                85                  90                  95

His Ala Ile Tyr Tyr Met Ser Tyr Ala Ser Leu Leu Glu Ser Lys Asn
            100                 105                 110

Lys Leu Arg Lys Ala Asn Glu Ile Phe Asp Leu Gly Ile
        115                 120                 125

<210> SEQ ID NO 13
<211> LENGTH: 125
<212> TYPE: PRT
<213> ORGANISM: Oryza sativa

<400> SEQUENCE: 13

Leu Leu Ala Ala Arg Arg Lys Met Ile Glu Ala Ile Asp Glu Tyr Ser
1               5                   10                  15

Gly Glu Asp Pro Leu Gln Pro Trp Ile Asp Cys Ile Lys Trp Val Gln
                20                  25                  30

Glu Ser Phe Pro Thr Gly Gly Asp Cys Ser Gly Leu Val Val Ile Tyr
            35                  40                  45

Glu Gln Cys Val Arg Ala Phe Trp His Asp Asp Arg Tyr Lys Asn Asp
        50                  55                  60

Leu Arg Tyr Leu Lys Val Trp Leu Glu Tyr Ala Gly Asn Cys Ala Asp
65                  70                  75                  80

Ser Glu Val Ile Phe Arg Phe Leu Glu Ala Asn Gln Ile Gly Gln Ser
                85                  90                  95

His Thr Asn Tyr Tyr Leu Ser Tyr Ala Ser Val Met Glu Ser Lys Asn
            100                 105                 110

Lys Leu Lys Lys Ala Asn Glu Ile Phe Asn Leu Gly Ile
        115                 120                 125

<210> SEQ ID NO 14
<211> LENGTH: 125
<212> TYPE: PRT
<213> ORGANISM: Brachypodium distachyon

<400> SEQUENCE: 14

Leu Leu Ala Glu Arg Arg Arg Met Ile Glu Ala Ile Glu Glu Tyr Gln
1               5                   10                  15

Gly Glu Asp Pro Leu Gln Pro Trp Val Asn Cys Ile Lys Trp Val Gln
                20                  25                  30

Glu Ser Phe Pro Ala Gly Gly Glu Ser Ser Gly Leu Val Val Ile Tyr
            35                  40                  45

Glu Gln Cys Val Arg Ala Phe Trp His Asp Glu Arg Tyr Lys Gly Asp
```

```
                50                  55                  60
Leu Arg Tyr Leu Lys Val Trp Leu Glu Tyr Ala Gly Asn Cys Ala Asp
 65                  70                  75                  80

Ala Glu Val Ile Phe Arg Phe Leu Glu Ala Asn Gln Ile Gly Asp Gly
                 85                  90                  95

His Ala Val Phe Tyr Ile His Tyr Ser Ser Leu Met Glu Ser Lys Asn
                100                 105                 110

Lys Leu Lys Lys Ala Asn Glu Ile Tyr Asn Leu Gly Ile
                115                 120                 125

<210> SEQ ID NO 15
<211> LENGTH: 125
<212> TYPE: PRT
<213> ORGANISM: Hordeum vulgare

<400> SEQUENCE: 15

Leu Leu Ala Glu Arg Arg Met Ile Glu Ala Ile Asp Glu Tyr Gln
 1               5                  10                  15

Gly Glu Asp Pro Leu Gln Pro Trp Val Asp Cys Ile Lys Trp Val Gln
                 20                  25                  30

Glu Ser Phe Pro Ala Gly Gly Glu Phe Ser Gly Leu Val Val Ile Tyr
                 35                  40                  45

Glu Gln Cys Val Arg Ala Phe Trp His Asp Glu Arg Tyr Lys Asp Asp
             50                  55                  60

Leu Arg Tyr Leu Lys Val Trp Leu Glu Tyr Ala Gly Asn Cys Ser Asp
 65                  70                  75                  80

Ala Glu Val Ile Phe Arg Phe Leu Glu Ser Asn Gln Ile Gly Glu Gly
                 85                  90                  95

His Ala Val Phe Tyr Ile Arg Tyr Ala Leu Leu Met Glu Ser Lys Asn
                100                 105                 110

Lys Leu Lys Lys Ala Asp Glu Ile Phe Val Leu Gly Ile
                115                 120                 125

<210> SEQ ID NO 16
<211> LENGTH: 129
<212> TYPE: PRT
<213> ORGANISM: Triticum aestivum

<400> SEQUENCE: 16

Leu Leu Ala Glu Arg Gly Arg Met Ile Gln Ala Ile Glu Glu Tyr Gln
 1               5                  10                  15

Gly Glu Asp Pro Leu Gln Pro Trp Val Asp Cys Ile Lys Trp Val Gln
                 20                  25                  30

Glu Ser Phe Pro Ala Gly Gly Glu Phe Ser Gly Leu Val Val Ile Tyr
                 35                  40                  45

Glu Gln Cys Val Arg Ala Phe Trp His Asp Glu Arg Tyr Lys Asp Asp
             50                  55                  60

Leu Arg Tyr Leu Lys Val Trp Leu Glu Tyr Phe Gly Leu Gln Ala Gly
 65                  70                  75                  80

Asn Cys Ser Asp Ala Glu Val Ile Phe Arg Phe Leu Glu Ser Asn Gln
                 85                  90                  95

Ile Gly Glu Gly His Ala Val Phe Tyr Ile Arg Tyr Ala Leu Leu Met
                100                 105                 110

Glu Ser Lys Asn Lys Leu Lys Lys Ala Asp Glu Ile Phe Asn Leu Gly
                115                 120                 125

Ile
```

```
<210> SEQ ID NO 17
<211> LENGTH: 129
<212> TYPE: PRT
<213> ORGANISM: Aegilops tauschii

<400> SEQUENCE: 17

Leu Leu Ala Glu Arg Arg Met Ile Glu Ala Thr Glu Glu Tyr Gln
1               5                   10                  15

Gly Glu Asp Pro Leu Gln Pro Trp Val Glu Cys Ile Lys Trp Val Gln
            20                  25                  30

Glu Ser Phe Pro Ala Gly Gly Glu Phe Ser Gly Leu Val Val Ile Tyr
        35                  40                  45

Glu Gln Cys Val Arg Ala Phe Trp His Asp Glu Arg Tyr Lys Asp Asp
    50                  55                  60

Leu Arg Tyr Leu Lys Val Trp Leu Glu Tyr Phe Gly Leu Gln Ala Gly
65                  70                  75                  80

Asn Cys Ser Asp Ala Glu Val Ile Phe Arg Phe Leu Gly Ser Asn Gln
                85                  90                  95

Ile Gly Glu Gly His Ala Val Phe Tyr Ile Arg Tyr Ala Ser Leu Met
            100                 105                 110

Glu Ser Lys Asn Lys Leu Lys Lys Ala Asp Glu Ile Phe Asn Leu Gly
        115                 120                 125

Ile

<210> SEQ ID NO 18
<211> LENGTH: 20
<212> TYPE: DNA
<213> ORGANISM: Zea mays

<400> SEQUENCE: 18
aggattctct gaagtggccc                                              20

<210> SEQ ID NO 19
<211> LENGTH: 20
<212> TYPE: DNA
<213> ORGANISM: Zea mays

<400> SEQUENCE: 19
cgctcctctt gctcctaact                                              20

<210> SEQ ID NO 20
<211> LENGTH: 22
<212> TYPE: DNA
<213> ORGANISM: Zea mays

<400> SEQUENCE: 20
agagccgtcc gtctgtatgt aa                                           22

<210> SEQ ID NO 21
<211> LENGTH: 20
<212> TYPE: DNA
<213> ORGANISM: Zea mays

<400> SEQUENCE: 21
cctttcgcgt ttgctttgta                                              20

<210> SEQ ID NO 22
<211> LENGTH: 24
<212> TYPE: DNA
```

```
<213> ORGANISM: Zea mays

<400> SEQUENCE: 22
gcatatgcga gatcatatcg ttga                                              24

<210> SEQ ID NO 23
<211> LENGTH: 24
<212> TYPE: DNA
<213> ORGANISM: Zea mays

<400> SEQUENCE: 23
ctatacagcc ctcagctctg ctgt                                              24
```

METHODS AND COMPOSITIONS FOR GENERATING DOUBLED HAPLOID PLANTS AND USE OF SAME IN BREEDING

CROSS-REFERENCE TO RELATED APPLICATIONS

This is a divisional application of U.S. Ser. No. 16/153,364, filed Oct. 5, 2018, which claims priority to provisional application U.S. Ser. No. 62/568,650, filed Oct. 5, 2017, both of which are incorporated herein by reference in their entirety.

SEQUENCE LISTING

The instant application contains a Sequence Listing which has been submitted in ASCII format by electronic submission and is hereby incorporated by reference in its entirety. Said ASCII copy, created on Sep. 17, 2021, is named LUBBERSTEDT_P12294US02_SEQLISTING_ST25.txt and is 36,328 bytes in size.

FIELD OF THE INVENTION

The present invention relates generally to plant molecular biology. More specifically, it relates to plants that have high frequency of spontaneous haploid genome doubling and related methods and uses for production of doubled haploid plants.

BACKGROUND OF THE INVENTION

Production of Doubled Haploids (DHs) in maize has become economically viable within the last 10 to 20 years. In a traditional DH program, a cross between two inbred parents is made to produce an F1. Then, the F1 is pollinated with a maternal haploid inducer to produce haploid kernels. Haploid kernels are chemically treated to induce genome doubling. Significant challenges in using DH technology in maize are efficiency of haploid induction, haploid selection, genome doubling, and seed production on chimeric haploid plants after colchicine treatment. The main bottleneck for making DH technology in maize more effective in terms of labor and costs is the genome doubling step. In most DH programs, a chemical treatment based on colchicine is used for genome doubling. Colchicine inhibits chromosome segregation during meiosis, leading to genome doubling. Colchicine is toxic. Therefore, proper precautions need to be taken for protection. The main issue in using colchicine (or other chemical treatments) is, that seedlings need to be treated before transplanting. It is thus very time consuming to first germinate seedlings, treat them for chromosome doubling, and then transplant them to the field, typically using a vegetable transplanter—in contrast to direct sowing of maize kernels.

Recently, genotypes with high levels of spontaneous haploid genome doubling (SHGD) have been reported in maize (e.g., Kleiber et al. 2012). Spontaneous haploid genome doubling occurs at an extreme low frequency, and leads to genome doubling in and thus fertility of haploids derived from genotypes with SHGD ability.

Implications of the present invention to a DH breeding program are substantial. It would remove greenhouse costs, transplanting, labor of treating haploids, and eliminate the need for the use of colchicine as a hazardous doubling agent. Putative haploids could be directly sown into the field without the need of genome doubling and associated costs. SHGD would make DH technology in maize more broadly available, which is still mostly confined to major breeding programs. The long-term goal is to dramatically increase efficiency and reduce costs of current DH procedures in maize by implementation of SHGD to facilitate DH line development. This will increase genetic gains of national and international maize breeding programs.

SUMMARY OF THE INVENTION

The inventors have identified QTLs which are associated with spontaneous haploid genome doubling (SHGD) in publicly available maize lines. According to the invention, a QTL has been identified on chromosome 5 near the centromere between markers 504_21 and (SEQ ID NOs: 20-21) p-umc2302F (SEQ ID NOs: 22-23), which may be used in marker-assisted selection of plants for breeding purposes. These markers have been shown to map close to the QTL and may be used in breeding to select for the spontaneous haploid genome doubling trait in maize. Thus, the present invention provides and includes a method for screening and selecting a maize plant comprising one or more QTL associated with spontaneous haploid genome doubling.

The present invention provides a method of introgressing an allele into a plant comprising (a) crossing at least one spontaneous haploid genome doubling maize plant with at least one second maize plant in order to form a population, (b) genotyping with at least one second maize plant in the population with respect to a maize genomic nucleic acid marker selected from the group of SEQ ID NOs: 20 through 23, and (c) selecting from the population at least one maize plant comprising at least one genotype corresponding to a spontaneous haploid genome doubling maize plant. In certain embodiments of this method, the population formed, genotyped, and selected from can be a segregating population. The invention further provides an elite maize plant produced by such method.

The genotyping is effected in step (b) by determining the allelic state of at least one of the maize genomic DNA markers. The allelic state is determined by an assay which is selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays.

The invention further provides a method of introgressing an allele into a maize plant comprising: (a) crossing at least one spontaneous haploid genome doubling maize plant with at least one non-spontaneous haploid genome doubling maize plant in order to form a population; (b) screening the population with at least one nucleic acid marker to determine if one or more maize plants from the population contains a spontaneous haploid genome doubling allele. In certain embodiments of this method, the population formed, genotyped, and selected from can be a segregating population.

The invention provides an elite maize plant obtained by such method, the maize plant comprising a nucleic acid molecule selected from the group of SEQ ID NOs: 20 through 23. The elite maize plant can exhibit a transgenic trait. Such transgenic trait is selected from the group consisting of herbicide tolerance, modified yield, insect control, fungal disease resistance, virus resistance, nematode resistance, bacterial disease resistance, mycoplasma disease resistance, starch production, starch modification, high oil production, modified oil production, modified fatty acid content, high protein production, germination and seedling growth control, plant growth and development, fruit ripening, enhanced animal and human nutrition, low raffinose, environmental stress resistance, increased digestibility, industrial enzymes, pharmaceutical peptides and secretable peptides and small molecules, improved digestibility, enzyme production, fiber production, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in maize.

The invention further provides assays for detecting spontaneous haploid genome doubling loci in a maize plant.

Methods of identifying maize plants comprising at least one allele associated with spontaneous haploid genome doubling are also provided. In certain embodiments of these methods of identifying a maize plant comprising at least one allele associated with spontaneous haploid genome doubling in a maize plant, the methods comprise: (a) genotyping at least one maize plant with at least one maize genomic nucleic acid marker selected from the group of SEQ ID NOs: 20-23, and (b) selecting at least one maize plant comprising an allele of at least one of the nucleic acid markers that is associated with spontaneous haploid genome doubling. In certain embodiments, the at least one maize plant genotyped in step (a) and/or the at least one maize plant selected in step (b) is a maize plant from a population generated by a cross. In certain embodiments, the selected one or more maize plants exhibit increased spontaneous haploid genome doubling. In embodiments where the population is generated by a cross, the cross can be of at least one spontaneous haploid genome doubling maize plant with at least one non-spontaneous haploid genome doubling. In still other embodiments, the methods can further comprise the step (c) of assaying the selected maize plant for spontaneous haploid genome doubling. In still other embodiments, the methods can further comprise the step of crossing the maize plant selected in step (b) to another maize plant. In still other embodiments, the methods can further comprise the step of obtaining seed from the maize plant selected in step (b).

Also provided herein are maize plants obtained by any of these methods of identifying maize plants comprising at least one allele associated with spontaneous haploid genome doubling. In certain embodiments, maize plants obtained by these methods can comprise an allele of at least one nucleic acid molecule selected from the group of SEQ ID NOs: 20 through 23 that is associated with spontaneous haploid genome doubling, and wherein the maize plant exhibits increased spontaneous haploid genome doubling. In certain embodiments, maize plants obtained by these methods are elite maize plants.

Methods of introgressing a spontaneous haploid genome doubling locus into a maize plant are also provided. In certain embodiments, these methods of introgressing a spontaneous haploid genome doubling locus into a maize plant comprise: (a) screening a population with at least one nucleic acid marker to determine if one or more maize plants from the population contains a spontaneous haploid genome doubling locus, and (b) selecting from the population at least one maize plant comprising an allele of the marker associated with the spontaneous haploid genome doubling locus. In certain embodiments of these methods, at least one of the markers is located within 5 cM, 2 cM, or 1 cM of the resistant allele. In other embodiments, at least one of the markers is located within 2 cM, or 1 cM of the resistant allele. In certain embodiments of these methods, at least one of the markers is located within 100 Kb of the resistance allele. In other embodiments, at least one of the markers is located within 1 Mb, or 1 Kb of the resistant allele. In certain embodiments of these methods, the population is a segregating population. In certain embodiments of these methods, at least one of the markers exhibits a LOD score of greater than 2.0 with the spontaneous haploid genome doubling locus. In other embodiments, at least one of the markers exhibits a LOD score of greater than 3.0 or greater than 4.0 with the spontaneous haploid genome doubling locus. In certain embodiments of these methods, at least one of the markers is selected from the group of SEQ ID NOs: 20-23.

Also provided herein are maize plants obtained by any of these methods of introgressing a spontaneous haploid genome doubling locus into a maize plant. In certain embodiments, a maize plant obtained by these methods can comprise an allele of at least one of nucleic acid marker selected from the group of SEQ ID NOs: 20-23 that is associated with spontaneous haploid genome doubling. In certain embodiments, a maize plant obtained by these methods can exhibit increased spontaneous haploid genome doubling.

In another embodiment, markers, such as single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al., 2003 Gen. Res. 13:513-523), microarray transcription profiles, DNA-derived sequences, and RNA-derived sequences that are genetically linked to or correlated with alleles of a QTL of the present invention can be utilized.

While not wishing to be bound by any theory, it is postulated that within the QTL region is a variant BUB1 gene. The invention thus includes a nucleic acid molecule, said molecule encoding a variant BUB1 protein that is associated with increased spontaneous haploid genome doubling. In one aspect, this invention relates to novel nucleic acid sequences encoding BUB1 or MAD3 variants that are associated with spontaneous haploid genome doubling and homologs thereof.

The B73 reference BUB1 nucleic acid sequence (SEQ ID NO: 2) and protein sequence (SEQ ID NO:4) are known and publicly available through GenBank (AQK69705). In certain embodiments the nucleic acid molecule comprises a nucleotide sequence which encodes a variant BUB1 protein. In one embodiment, the BUB1 variant nucleic acid sequence includes one or more mutations that increase frequency of spontaneous haploid genome doubling. Thus, the invention includes variant BUB1 nucleic acid sequences having one or more of the following mutations: T7G, C242T, C373A, C522T, C673A, A716T, G1021A, T1022C, T1092C, and G1179T as determined by reference to the B73 BUB1 coding sequence (SEQ ID NO: 6). In one embodiment the BUB1 variant nucleotide sequence has all of the mutations.

In one embodiment, the BUB1 variant protein sequence includes one or more mutations that increase frequency of spontaneous haploid genome doubling. The invention includes variant BUB1 proteins having one or more of the following mutations: L3V, A81V, L125M, L225M, D239V, V341T, and Q393H as determined by reference to the B73 protein sequence (SEQ ID NO: 4). In one embodiment, the BUB1 variant protein has all of the mutations.

In one embodiment, the variant BUB1 is the nucleic acid sequence set forth in SEQ ID NO: 1 or SEQ ID NO: 5. In another embodiment, the variant BUB1 comprises a nucleic acid sequence having at least about 80%, at least about 90%, at least about 95%, at least about 98%, at least about 99%, about 99.5% or more sequence identity to SEQ ID NO: 1 or SEQ ID NO: 5. The BUB1 variant nucleotide sequences include one or more mutations that increase frequency of spontaneous haploid genome doubling. In some embodiments, the variant BUB1 nucleic acid sequence includes at least one base change so as not to be a naturally occurring sequence. In another embodiment, the polynucleotide includes at least one base change so as not to be the genomic sequence as present in GF1 SGHD phenotypes (SEQ ID NO:1).

The invention includes a nucleic acid molecule, said molecule encoding a variant BUB1 protein that is associated with increased spontaneous haploid genome doubling wherein said nucleic acid molecule comprises a nucleotide sequence selected from the group consisting of:

(a) a polynucleotide, having at least about 80%, at least about 90%, at least about 95%, at least about 98%, at least about 99%, about 99.5% or more sequence identity to SEQ ID NO: 1 or 5;

(b) a polynucleotide, or a complement thereof, encoding a polypeptide sequence of SEQ ID NO: 3, or conservatively modified variants thereof; and (c) a polynucleotide, or a complement thereof, that hybridizes under stringent conditions over substantially the entire length of a polynucleotide subsequence comprising at least 100 contiguous nucleotides of SEQ ID NO: 1 or 5, or that hybridizes to a polynucleotide sequence of (a) or (b). The polynucleotides include one or more mutations that increase the frequency of spontaneous haploid genome doubling. In some embodiments the polynucleotide includes at least one base change so as not to be the genomic sequence as present in GF1 SGHD phenotypes (SEQ ID NO:1).

The invention also includes nucleic acid constructs comprising the nucleic acid molecules of the invention operably linked to a promoter that drives expression in a plant cell. The invention further includes vectors, cells and plants comprising the same. In some embodiments, the construct is an inhibition construct, in some embodiments the construct is an expression construct, in some embodiments the construct is a construct designed for gene editing.

The invention also includes an isolated polypeptide capable of increasing spontaneous haploid doubling comprising. In one embodiment, the BUB1 variant polypeptide include one or more mutations that increase frequency of spontaneous haploid genome doubling. In another embodiment, a variant BUB1 protein comprises one or more amino acid substitutions in a MAD3/BUB1 domain. In some embodiments, the polypeptide comprises a sequence having one or more of the following mutations: L3V, A81V, L125M, L225M, D239V, V341T, and Q393H as determined by reference to the B73 protein sequence (SEQ ID NO: 4).

In yet another embodiment the polypeptides of the invention comprise an amino acid sequence selected from the group consisting of: (a) the amino acid sequence comprising SEQ ID NO: 3; (b) the amino acid sequence comprising at least 80%, 90%, 95%, 98%, or 99% sequence identity to SEQ ID NO: 3, wherein said polypeptide has the ability to increase spontaneous haploid doubling; and, (c) the amino acid sequence comprising at least 20 consecutive amino acids of SEQ ID NO: 3, wherein said polypeptide retains the ability to increase spontaneous haploid doubling. In certain embodiments, the polypeptide includes one or more amino acid substitutions so that the protein is not the naturally occurring protein of SEQ ID NO: 3.

In yet another embodiment of the invention methods of creating a modified plant with increased spontaneous haploid genome doubling as compared to a non-modified plant, by modulating the activity of one or more spindle assembly checkpoint polypeptides. In a preferred embodiment, the polypeptide is a BUB1/MAD3 protein. In some embodiments, BUB1/MAD3 protein includes one or more amino acid substitutions that are associated with increased haploid genome doubling. In some embodiments the activity of the one or more BUB1/MAD3 proteins is increased, in other instances the activity may be decreased. In certain embodiments a plant may be transformed with a heterologous nucleic acid to introduce a modulated BUB1/MAD3 protein. This can include methods to introduce mutations into native BUB1/MAD3 genomic sequences, such as by homologous recombination, gene editing and the like, or to introduce an expression construct to express a modified BUB1/MAD3 protein, or to simple introduce the heterologous protein to the plant directly, such as through seed or plant treatments.

In another aspect of the present invention, nucleic acid constructs and transformation vectors comprising the identified and isolated nucleotide sequences are disclosed. The transformation vectors can be used to transform plants to increase the frequency of spontaneous haploid genome doubling in transformed cells. Transformed cells as well as regenerated transgenic plants and seeds containing and expressing the isolated and identified DNA sequences and protein products are also provided.

Another aspect of the invention provides methods of producing a double haploid plant without toxic chromosomal doubling agents with the plants of the invention. Another aspect of the invention, disclosed herein are methods of breeding plants of the invention and resultant plants, varieties, hybrids, and inbreds developed therefrom. The present invention includes and provides methods of introgressing the increased spontaneous haploid genome doubling trait into a second maize germplasm comprising crossing a first maize germplasm with a second maize germplasm to introgress the variant BUB1/MAD3 genomic sequence into the genome of the second maize germplasm. In another embodiment, backcrosses and selections can be performed.

In yet another embodiment a method of identifying a plant which has increased spontaneous haploid genome doubling is disclosed by assaying for the presence of a variant BUB1/MAD3 protein or nucleic acid sequence.

The plants in accordance with the present invention, in a non-limiting example, may be maize, rice, wheat, barley, oats, rye, millet, sorghum, tobacco, tomato, potato, soybean, canola, alfalfa, sunflower, and cotton. In a preferred embodiment, the plant is maize.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

Figure 1C:
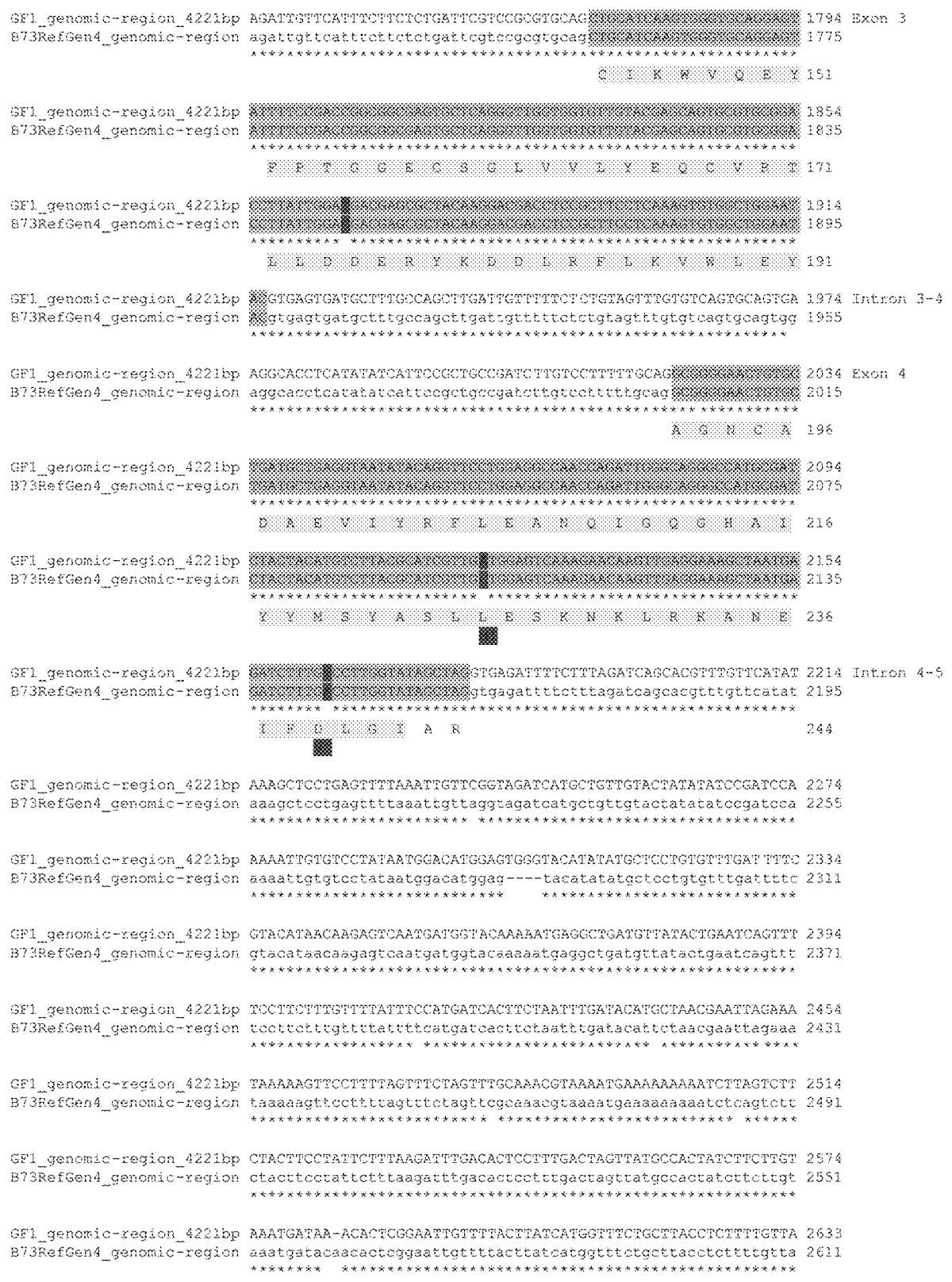

FIGS. 1A-1E show a multiple sequence alignment of BUBR1 genomic DNA sequences for the GF1 SHGD allele and the B73 reference non-doubling allele (SEQ ID NOs: 1, 2 and 4).

FIG. 2 shows a multiple sequence alignment of the GF1 SHGD protein sequence and the B73 reference non-doubling protein sequence (SEQ ID NOs: 3-4).

FIG. 3 shows a comparison of the MAD-BUB1 domain in GF1, B73, PH207, other Poaceae, and *Arabidopsis* (SEQ ID NOs: 7-17).

DETAILED DESCRIPTION OF THE INVENTION

The following definitions and introductory matters are provided to facilitate an understanding of the present invention.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. In describing the present invention, the following terms will be employed, and are intended to be defined as indicated below.

As used herein, "BUBR1" shall be interpreted to mean BUB1-related and refers to the mitotic spindle checkpoint serine/threonine-protein kinase BUB1 (budding uninhibited by benzymidazol 1), also known as MAD3 (mitotic arrest deficient 3). The term "BUBR1" is used interchangeably herein with "BUB1/MAD3". The term "BUBR1" as used herein encompasses any Mad3/BUB1 domain containing protein. Non-limiting examples of BUBR1 nucleic acid sequences can be found in *Zea mays* (GRMZM2G009913), *Oryza sativa* (LOC_Os02g10020), *Arabidopsis thaliana* (AT2G33560), *Setaria viridis* (Sevir. 1G051800), *Brachypodium distachyon* (Bradi3g06840), *Solanum lycopersicum* (Solyc04g082900). Additionally, other BUBR1 homologs may be identified through databases such as Genbank.

As used herein, "GF1", "GF2", "GF3" and "GF6" refer to public and expired Plant Variety Protection inbred lines. The cultivar names for the lines are 'A427', 'A673', 'CR1HT' (PVP 8400042), and '788' (PVP 8700045), respectively. The line 'A427' is a publicly available non-stiff stalk inbred line developed out of the University of Minnesota. The lines are available from sources known to those of ordinary skill in the art including, for example, the USDA National Plant Germplasm System.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" or "isolated nucleic acid" or "isolated protein" refer to material, such as a nucleic acid or a protein, which is substantially or essentially free from components which normally accompany or interact with it as found in its naturally occurring environment. The isolated material optionally comprises material not found with the material in its natural environment. Nucleic acids which are "isolated", as defined herein, are also referred to as "heterologous" nucleic acids.

"Regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory elements may include, but are not limited to, promoters, translation leader sequences, introns, and polyadenylation recognition sequences. Regulatory elements present on a recombinant DNA construct that is introduced into a cell can be endogenous to the cell, or they can be heterologous with respect to the cell. The terms "regulatory element" and "regulatory sequence" are used interchangeably herein.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

As used herein, "vector" includes reference to a nucleic acid used in transfection of a host cell and into which can be inserted a polynucleotide. Vectors are often replicons. Expression vectors permit transcription of a nucleic acid inserted therein.

A "homologous", "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively.

Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. GenBank® is the recognized United States-NIH genetic sequence database, comprising an annotated collection of publicly available DNA sequences, and which further incorporates submissions from the European Molecular Biology Laboratory (EMBL) and the DNA DataBank of Japan (DDBJ), see Nucleic Acids Research, January 2013, v 41(D1) D36-42 for discussion. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein, for instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) Proc. Natl. Acad. Sci. USA 82:2306-9), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "genetically modified" with reference to a cell, callus, tissue, plant, or animal which has been altered "by the hand of man." A genetically modified cell, callus, tissue, plant, or animal has had an exogenous polynucleotide introduced thereto and includes progeny cells derived therefrom. Genetically modified, also refers to a cell callus, tissue, plant or animal that has been genetically manipulated such that endogenous nucleotides have been altered to include a mutation, such as a deletion, an insertion, a transition, a transversion, or a combination thereof, such as by gene editing. For instance, an endogenous coding region could be deleted. Such mutations may result in a polypeptide having a different amino acid sequence than was encoded by the endogenous polynucleotide. Another example of a genetically modified cell, callus, tissue, plant, or animal is one having an altered regulatory sequence, such as a promoter, to result in increased or decreased expression of an operably linked endogenous coding region.

As used herein, "control plant" is a plant without recombinant DNA disclosed herein. A control plant is used to measure and compare trait improvement in a transgenic plant with such recombinant DNA. A suitable control plant may be a non-transgenic plant of the parental line used to generate a transgenic plant herein. Alternatively, a control plant may be a transgenic plant that comprises an empty vector or marker gene, but does not contain the recombinant DNA that produces the trait improvement. A control plant may also be a negative segregant progeny of hemizygous transgenic plant.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is maize.

As used herein, the term "maize" means *Zea mays* or corn and includes all plant varieties that can be bred with corn, including wild maize species.

As used herein, the term "elite line" means any line that has resulted from breeding and selection for superior agronomic performance.

As used herein, a plant referred to as "haploid" has a single set (genome) of chromosomes and the reduced number of chromosomes (n) in the haploid plant is equal to that of the gamete.

As used herein, a plant referred to as "diploid" has two sets (genomes) of chromosomes and the chromosome number (2n) is equal to that of the zygote.

As used herein, a plant referred to as "doubled haploid" is developed by doubling the haploid set of chromosomes. A plant or seed that is obtained from a doubled haploid plant that is selfed to any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes; that is, a plant will be considered doubled haploid if it contains viable gametes, even if it is chimeric.

The terms "haploid male fertility" (HMF) and "spontaneous haploid genome doubling" (SHGD) are used interchangeably herein, as HMF is the main bottleneck for deriving DH plants after self-pollination. SHGD ability in a sense of enabling self-pollination requires both male and female fertility, the latter not usually being a limitation in maize haploids.

As used herein, an "inducer" is a line which is crossed with another line and promotes the formation of haploid embryos. Haploid inducer plants produce pollen which when crossed onto non-inducer germplasm results in the gynogenic development of haploid seeds. Non-limiting examples of inducer lines for maize include Stock 6, KMS, ZMS, WS14, KEMS, MHI, RWS, UH400, PK6, HZI1, CAUHOI, and PHI.

The initial step in the production of haploid seeds from a hybrid or segregating maternal parent plant derives from the pollination with pollen from a haploid inducer on to the ear from a seed producing plant. A result of this hybridization process is the production of diploid and maternal haploid (1n) kernels. The induced haploid (1n) kernels are often distinguished from the diploid seed by the use of color markers which indicate embryo ploidy. The diploid seeds are generally discarded, while haploid kernels or embryos are often subjected to genome doubling processes to produce doubled haploid plants.

Homozygous doubled haploid plants can be regenerated from haploid cells by contacting the haploid cells, including but not limited to haploid callus, with genome doubling agents, such as colchicine, anti-microtubule herbicides, or nitrous oxide to create homozygous doubled haploid cells. The plants of the present invention undergo spontaneous haploid genome doubling at a high frequency and do not require the use of a genome doubling agent.

The doubled haploid plant is allowed to mature and the resulting doubled haploid seeds when planted will produce homozygous plants (also called inbred plant or lines) These inbred lines are the materials that breeders utilize to pursue their hybrid development programs. Doubled haploid plants can be further crossed to other plants to generate F1, F2, or subsequent generations of plants with desired traits.

As used herein, "targeted genome modification" or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customizable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate its nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (1-111) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Cas9 is thus the hallmark protein of the type II CRISPR-Cas system, and a large monomeric DNA nuclease guided to a DNA target sequence adjacent to the PAM (protospacer adjacent motif) sequence motif by a complex of two non-coding RNAs:CRIPSR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3. Cas9 expression plasmids for use in the methods of the invention can be constructed as described in the art.

Breeding Plants

In addition to direct transformation of a particular plant genotype with a construct prepared according to the current invention, transgenic plants may be made by crossing a plant having a selected DNA of the invention to a second plant lacking the construct. For example, a selected polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Unless context dictates otherwise, the descriptions and definitions of the features set out above are not limited to any particular aspect or embodiment of the invention and apply equally to all aspects and embodiments which are described.

Nucleic Acids

The present invention provides, inter alia, isolated nucleic acids of RNA, DNA, homologs, paralogs and orthologs and/or chimeras thereof, comprising a BUBR1 polynucleotide or protein encoded thereby. This includes naturally occurring as well as synthetic variants and homologs of the sequences.

Sequences homologous, i.e., that share significant sequence identity or similarity, to those provided herein are also an aspect of the invention. Homologous sequences can be derived from any plant including monocots and dicots and in particular agriculturally important plant species, including but not limited to, crops such as soybean, wheat, corn (maize), potato, cotton, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte, related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

For example, a clade of very similar MADS domain transcription factors from *Arabidopsis* all share a common function in flowering time (Ratcliffe et al. (2001) Plant Physiol. 126: 122-132), and a group of very similar AP2 domain transcription factors from *Arabidopsis* are involved in tolerance of plants to freezing (Gilmour et al. (1998) Plant J. 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Variant Nucleotide Sequences in the Non-Coding Regions

The BUBR1 nucleotide sequences are used to generate variant nucleotide sequences having the nucleotide sequence of the 5'-untranslated region, 3'-untranslated region, or promoter region that is approximately 70%, 75%, and 80%, 85%, 90% and 95% identical to the original nucleotide sequence. These variants are then associated with natural variation in the germplasm for component traits related to spontaneous haploid genome doubling. The associated variants are used as marker haplotypes to select for the desirable traits.

Variant Amino Acid Sequences of Polypeptides

Variant amino acid sequences of the BUBR1 polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to spontaneous haploid genome doubling. The associated variants are used as marker haplotypes to select for the desirable traits.

The present invention also includes polynucleotides optimized for expression in different organisms. For example, for expression of the polynucleotide in a particular plant, the sequence can be altered to account for specific codon.

The BUBR1 nucleic acids which may be used for the present invention comprise isolated BUBR1 polynucleotides which are inclusive of:
(a) a polynucleotide, having at least about 80%, at least about 90%, at least about 95%, at least about 98%, at least about 99%, about 99.5% or more sequence identity to SEQ ID NO: 1 or 5;
(b) a polynucleotide, or a complement thereof, encoding a polypeptide sequence of SEQ ID NO: 3, or conservatively modified variants thereof;
(c) a polynucleotide, or a complement thereof, that hybridizes under stringent conditions over substantially the entire length of a polynucleotide subsequence comprising at least 100 contiguous nucleotides of SEQ ID NO: 1 or 5, or that hybridizes to a polynucleotide sequence of (a) or (b); and
(d) a polynucleotide that is at least about 85% identical to a polynucleotide sequence of (a), (b) or (c).

In some embodiments the polynucleotide includes at least one base change so as not to be the genomic sequence as present in GF1 SGHD phenotypes (SEQ ID NO:1).

In one embodiment, nucleic acid-based analyses for the presence or absence of the genetic polymorphism can be used for the selection of seeds in a breeding population. A wide variety of genetic markers for the analysis of genetic polymorphisms are available and known to those of skill in the art. The analysis may be used to select for genes, QTL, alleles, or genomic regions (haplotypes) that comprise or are linked to a genetic marker.

Herein, nucleic acid analysis methods are known in the art and include, but are not limited to, PCR-based detection methods (for example, TaqMan assays), microarray methods, and nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al., 1986 Cold Spring Harbor Symp. Quant. Biol. 51:263-273; European Patent No. 50,424; European Patent No. 84,796; European Patent No. 258,017; European Patent No. 237,362; European Patent No. 201,184; U.S. Pat. Nos. 4,683,202; 4,582,788; and 4,683,194), using primer pairs that are capable of hybridizing to the proximal sequences that define a polymorphism in its double-stranded form.

Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in maize genomic DNA samples. These maize genomic DNA samples used include but are not limited to, maize genomic DNA isolated directly from a maize plant, cloned maize genomic DNA, or amplified maize genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464 employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of corn genomic DNA which flanks a region containing the polymorphism to be assayed. Following amplification of the region of the corn genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In a preferred method for detecting polymorphisms, SNPs and Indels can be detected by methods disclosed in U.S. Pat. Nos. 5,210,015; 5,876,930; and 6,030,787 in which an oligonucleotide probe having a 5'fluorescent reporter dye and a 3'quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

For the purpose of QTL mapping, the markers included should be diagnostic of origin in order for inferences to be made about subsequent populations. SNP markers are ideal for mapping because the likelihood that a particular SNP allele is derived from independent origins in the extent populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al., (Lander et al., 1989 Genetics, 121:185-199), and the interval mapping, based on maximum likelihood methods described therein, and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emers.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation. Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

The development of new elite corn hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of Crop Improvement," Longman, Inc., NY, 369-399, 1979; Sneep and Hendriksen, "Plant Breeding Perspectives," Wageningen (ed), Center for Agricultural Publishing and Documentation, 1979; Fehr, In: Soybeans: Improvement, Production and Uses, 2nd Edition, Manograph, 16:249, 1987; Fehr, "Principles of Variety Development," Theory and Technique, (Vol. 1) and Crop Species Soybean (Vol. 2), Iowa State Univ., Macmillan Pub. Co., NY, 360-376, 1987).

An alternative to traditional QTL mapping involves achieving higher resolution by mapping haplotypes, versus individual markers (Fan et al., 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well within the skill of the ordinary practitioner of the art.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, IL).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in rice. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered Km and/or Kcat over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present disclosure further provides recombinant expression cassettes comprising a nucleic acid of the present disclosure. A nucleic acid sequence coding for the desired polynucleotide of the present disclosure, for example a cDNA or a genomic sequence encoding a polypeptide long enough to code for an active protein of the present disclosure, can be used to construct a recombinant expression cassette which can be introduced into the desired host cell. A recombinant expression cassette will typically comprise a polynucleotide of the present disclosure operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

Promoters, Terminators, Introns

A plant promoter fragment can be employed which will direct expression of a polynucleotide of the present disclosure in essentially all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) Nature 313:810-2; rice actin (McElroy, et al., (1990) Plant Cell 163-171); ubiquitin (Christensen, et al., (1992) Plant Mol. Biol. 12:619-632 and Christensen, et al., (1992) Plant Mol. Biol. 18:675-89); pEMU (Last, et al., (1991) Theor. Appl. Genet. 81:581-8); MAS (Velten, et al., (1984) EMBO J. 3:2723-30) and maize H3 histone (Lepetit, et al., (1992) Mol. Gen. Genet. 231:276-85 and Atanassvoa, et al., (1992) Plant Journal 2(3):291-300); ALS promoter, as described in PCT Application Number WO 1996/30530 and other transcription initiation regions from various plant genes known to those of skill. For the present disclosure ubiquitin is the preferred promoter for expression in monocot plants.

Alternatively, the plant promoter can direct expression of a polynucleotide of the present disclosure in a specific tissue or may be otherwise under more precise environmental or developmental control. Such promoters may be "inducible" promoters. Environmental conditions that may affect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light. Diurnal promoters that are active at different times during the circadian rhythm are also known (US Patent Application Publication Number 2011/0167517, incorporated herein by reference).

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) Nucleic Acids Res. 12:369-85); the potato proteinase inhibitor II (PINII) gene (Keil, et al., (1986) Nucleic Acids Res. 14:5641-50 and An, et al., (1989) Plant Cell 1:115-22) and the CaMV 19S gene (Mogen, et al., (1990) Plant Cell 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) Mol. Cell Biol. 8:4395-4405; Callis, et al., (1987) Genes Dev. 1:1183-200). Such intron enhancement of gene expression is typically greatest when placed near the 5' end of the transcription unit. Use of maize introns Adh1-S intron 1, 2 and 6, the Bronze-1 intron are known in the art. See generally, The Maize Handbook, Chapter 116, Freeling and Walbot, eds., Springer, New York (1994).

Signal Peptide Sequences

Plant signal sequences, including, but not limited to, signal-peptide encoding DNA/RNA sequences which target proteins to the extracellular matrix of the plant cell (Dratewka-Kos, et al., (1989) J. Biol. Chem. 264:4896-900), such as the *Nicotiana plumbaginifolia* extension gene (DeLoose, et al., (1991) Gene 99:95-100); signal peptides which target proteins to the vacuole, such as the sweet potato sporamin gene (Matsuka, et al., (1991) Proc. Natl. Acad. Sci. USA 88:834) and the barley lectin gene (Wilkins, et al., (1990) Plant Cell, 2:301-13); signal peptides which cause proteins to be secreted, such as that of PRIb (Lind, et al., (1992) Plant Mol. Biol. 18:47-53) or the barley alpha amylase (BAA) (Rahmatullah, et al., (1989) Plant Mol. Biol. 12:119) or signal peptides which target proteins to the plastids such as that of rapeseed enoyl-Acp reductase (Verwaert, et al., (1994) Plant Mol. Biol. 26:189-202) are useful in the disclosure.

Markers

The vector comprising the sequences from a polynucleotide of the present disclosure will typically comprise a marker gene, which confers a selectable phenotype on plant cells. The selectable marker gene may encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Also useful are genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Constructs described herein may comprise a polynucleotide of interest encoding a reporter or marker product. Examples of suitable reporter polynucleotides known in the art can be found in, for example, Jefferson, et al., (1991) in Plant Molecular Biology Manual, ed. Gelvin, et al., (Kluwer Academic Publishers), pp. 1-33; DeWet, et al. (1987) Mol. Cell. Biol. 7:725-737; Goff, et al., (1990) EMBO J. 9:2517-2522; Kain, et al., (1995) Bio Techniques 19:650-655 and Chiu, et al., (1996) Current Biology 6:325-330. In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate and phosphinothricin.

In some embodiments, the expression cassettes disclosed herein comprise a polynucleotide of interest encoding scorable or screenable markers, where presence of the polynucleotide produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments, such as the maize C1 and C2, the B gene, the p1 gene and the bronze locus genes, among others. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP) and DsRed2 (Clontechniques, 2001) where plant cells transformed with the marker gene are red in color, and thus visually selectable. Additional examples include a p-lactamase gene encoding an enzyme for which various chromogenic substrates are known (e.g., PADAC, a chromogenic cephalosporin), a xy1E gene encoding a catechol dioxygenase that can convert chromogenic catechols, an α-amylase gene and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) Biotechnol Bioeng 85:610-9 and Fetter, et al., (2004) Plant Cell 16:215-28), cyan florescent protein (CYP) (Bolte, et al., (2004) J. Cell Science 117:943-54 and Kato, et al., (2002) Plant Physiol 129:913-42) and yellow florescent protein (PhiYFP® from Evrogen, see, Bolte, et al., (2004) J. Cell Science 117:943-54). For additional selectable markers, see generally, Yarranton, (1992) Curr. Opin. Biotech. 3:506-511; Christopherson, et al., (1992) Proc. Natl. Acad. Sci. USA 89:6314-6318; Yao, et al., (1992) Cell 71:63-72; Reznikoff, (1992) Mol. Microbiol. 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc. Natl. Acad. Aci. USA 86:5400-5404; Fuerst, et al., (1989) Proc. Natl. Acad. Sci. USA 86:2549-2553; Deuschle, et al., (1990) Science 248:480-483; Gossen, (1993) Ph.D. Thesis, University of Heidelberg; Reines, et al., (1993) Proc. Natl. Acad. Sci. USA 90:1917-1921; Labow, et al., (1990) Mol. Cell. Biol. 10:3343-3356; Zambretti, et al., (1992) Proc. Natl. Acad. Sci. USA 89:3952-3956; Bairn, et al., (1991) Proc. Natl. Acad. Sci. USA 88:5072-5076; Wyborski, et al., (1991) Nucleic Acids Res. 19:4647-4653; Hillenand-Wissman, (1989) Topics Mol. Struc. Biol. 10:143-162; Degenkolb, et al., (1991) Antimicrob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-919; Hlavka, et al., (1985) Handbook of Experimental Pharmacology, Vol. 78 (Springer-Verlag, Berlin); Gill, et al., (1988) Nature 334:721-724. Such disclosures are herein incorporated by reference. The above list of selectable marker genes is not meant to be limiting. Any selectable marker gene can be used in the compositions and methods disclosed herein.

Typical vectors useful for expression of genes in higher plants are well known in the art and include vectors derived from the tumor-inducing (Ti) plasmid of *Agrobacterium tumefaciens* described by Rogers, et al., (1987) Meth. Enzymol. 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) Gene 61:1-11 and Berger, et al., (1989) Proc. Natl. Acad. Sci. USA, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

In additional embodiments, enhancer elements may be introduced which increase expression of the polynucleotides of the invention.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HAS tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas ($7^{th}$ ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the BUBR1 gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert a BUBR1 polynucleotide into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. G. P. Chapman, et al., pp. 197-209. Longman, N Y (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) Nature 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic pl embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 µm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$) precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC,* A2-38, p. 53; D'Halluin, et al., (1992) *Plant Cell* 4:1495-505; and Spencer, et al., (1994) *Plant Mol. Biol.* 24:51-61.

Reducing the Activity of a BUBR1 Polypeptide

In certain embodiments the invention may include modulation of the BUBR1 gene to reduce or eliminate the activity of an BUBR1 polypeptide, perhaps during certain developmental stages or tissues etc., by transforming a plant cell with an expression cassette that expresses a polynucleotide that inhibits the expression of the BUBR1 polypeptide. The polynucleotide may inhibit the expression of the BUBR1 polypeptide directly, by preventing transcription or translation of the BUBR1 messenger RNA, or indirectly, by encoding a polypeptide that inhibits the transcription or translation of an BUBR1 gene encoding a BUBR1 polypeptide. Methods for inhibiting or eliminating the expression of a gene in a plant are well known in the art, and any such method may be used in the present invention to inhibit the expression of the BUBR1 polypeptide. Many methods may be used to reduce or eliminate the activity of an BUBR1 polypeptide. In addition, more than one method may be used to reduce the activity of a single BUBR1 polypeptide.

1. Polynucleotide-Based Methods:

In some embodiments of the present invention, a plant is transformed with an expression cassette that is capable of expressing a polynucleotide that inhibits the expression of a BUBR1 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one BUBR1 polypeptide is an expression cassette capable of producing an RNA molecule that inhibits the transcription and/or translation of at least one BUBR1 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a BUBR1 polypeptide are given below.

i. Sense Suppression/Cosuppression

In some embodiments of the invention, inhibition of the expression of an BUBR1 polypeptide may be obtained by sense suppression or cosuppression. For cosuppression, an expression cassette is designed to express an RNA molecule corresponding to all or part of a messenger RNA encoding a BUBR1 polypeptide in the "sense" orientation. Over expression of the RNA molecule can result in reduced expression of the native gene. Accordingly, multiple plant lines transformed with the cosuppression expression cassette are screened to identify those that show the greatest inhibition of BUBR1 polypeptide expression.

The polynucleotide used for cosuppression may correspond to all or part of the sequence encoding the BUBR1 polypeptide, all or part of the 5' and/or 3' untranslated region of an BUBR1 polypeptide transcript, or all or part of both the coding sequence and the untranslated regions of a transcript encoding a BUBR1 polypeptide. In some embodiments where the polynucleotide comprises all or part of the coding region for the BUBR1 polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323; herein incorporated by reference.

ii. Antisense Suppression

In some embodiments of the invention, inhibition of the expression of the BUBR1 polypeptide may be obtained by antisense suppression. For antisense suppression, the expression cassette is designed to express an RNA molecule complementary to all or part of a messenger RNA encoding the BUBR1 polypeptide. Over expression of the antisense RNA molecule can result in reduced expression of the native gene. Accordingly, multiple plant lines transformed with the antisense suppression expression cassette are screened to identify those that show the greatest inhibition of BUBR1 polypeptide expression.

The polynucleotide for use in antisense suppression may correspond to all or part of the complement of the sequence encoding the BUBR1 polypeptide, all or part of the complement of the 5' and/or 3' untranslated region of the BUBR1 transcript, or all or part of the complement of both the coding sequence and the untranslated regions of a transcript encoding the BUBR1 polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

iii. Double-Stranded RNA Interference

In some embodiments of the invention, inhibition of the expression of a BUBR1 polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of BUBR1 polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of a BUBR1 polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731; and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and U.S. Patent Publication No. 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and U.S. Patent Publication No. 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J* 19:5194-5201;

Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the BUBR1 polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362, and U.S. Pat. No. 6,635,805, each of which is herein incorporated by reference.

vi. Ribozymes

In some embodiments, the polynucleotide expressed by the expression cassette of the invention is catalytic RNA or has ribozyme activity specific for the messenger RNA of the BUBR1 polypeptide. Thus, the polynucleotide causes the degradation of the endogenous messenger RNA, resulting in reduced expression of the BUBR1 polypeptide. This method is described, for example, in U.S. Pat. No. 4,987,071, herein incorporated by reference.

vii. Small Interfering RNA or Micro RNA

In some embodiments of the invention, inhibition of the expression of BUBR1 polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of BUBR1 expression, the 22-nucleotide sequence is selected from an BUBR1 transcript sequence and contains 22 nucleotides of said BUBR1 sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a BUBR1 polypeptide, resulting in reduced expression of the gene. In particular embodiments, the zinc finger protein binds to a regulatory region of a BUBR1 gene. In other embodiments, the zinc finger protein binds to a messenger RNA encoding a BUBR1 polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355; each of which is herein incorporated by reference.

3. Polypeptide-Based Inhibition of Protein Activity

In some embodiments of the invention, the polynucleotide encodes an antibody that binds to at least one BUBR1 polypeptide, and reduces the activity of the BUBR1 polypeptide. In another embodiment, the binding of the antibody results in increased turnover of the antibody-BUBR1 complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an BUBR1 polypeptide may be reduced or eliminated by disrupting the gene encoding the BUBR1 polypeptide. The gene encoding the BUBR1 polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have desired traits.

i. Transposon Tagging

In one embodiment of the invention, transposon tagging is used to reduce or eliminate the BUBR1 activity of one or more BUBR1 polypeptides. Transposon tagging comprises inserting a transposon within an endogenous BUBR1 gene to reduce or eliminate expression of the BUBR1 polypeptide. "BUBR1 gene" is intended to mean the gene that encodes a BUBR1 polypeptide.

In this embodiment, the expression of one or more BUBR1 polypeptides is reduced or eliminated by inserting a transposon within a regulatory region or coding region of the gene encoding the BUBR1 polypeptide. A transposon that is within an exon, intron, 5' or 3' untranslated sequence, a promoter, or any other regulatory sequence of a BUBR1 gene may be used to reduce or eliminate the expression and/or activity of the encoded BUBR1 polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant BUBR1 polypeptides suitable for mutagenesis with the goal to eliminate BUBR1 activity have been described. Such mutants can be isolated according to well-known procedures, and mutations in different BUBR1 loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more BUBR1 polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

Method of Use for BUBR1 Polynucleotides, Expression Cassettes, and Additional Polynucleotides The nucleotides, expression cassettes and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703, 049); barley high lysine (Williamson, et al., (1987) Eur. J. Biochem. 165:99-106; and WO 98/20122); and high methionine proteins (Pedersen, et al., (1986) J. Biol. Chem. 261: 6279; Kirihara, et al., (1988) Gene 71:359; and Musumura, et al., (1989) Plant Mol. Biol. 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,736,514; 5,723,756; 5,593,881; Geiser, et al., (1986) Gene 48:109); lectins (Van Damme, et al., (1994) Plant Mol. Biol. 24:825); fumonisin detoxification genes (U.S. Pat. No. 5,792,931); avirulence and disease resistance genes (Jones, et al., (1994) Science 266:789; Martin, et al., (1993) Science 262:1432; Mindrinos, et al., (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) J. Bacteriol. 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane H+-ATPase (MHA2) (Frias, et al., (1996) Plant Cell 8:1533-44); AKT1, a component of the potassium uptake apparatus in *Arabidopsis*, (Spalding, et al., (1999) J Gen Physiol 113:909-18); RML genes which activate cell division cycle in the root apical cells (Cheng, et al., (1995) Plant Physiol 108:881); maize glutamine synthetase genes (Sukanya, et al., (1994) Plant Mol Biol 26:1935-46) and hemoglobin (Duff, et al., (1997) J. Biol. Chem 27:16749-16752, Arredondo-Peter, et al., (1997) Plant Physiol. 115:1259-1266; Arredondo-Peter, et al., (1997) Plant Physiol 114:493-500 and references sited therein). The sequence of interest may also be useful in expressing antisense nucleotide sequences of genes that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990, 389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) Eur. J. Biochem. 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) Proceedings of the World Congress on Vegetable Protein Utilization in Human Foods and Animal Feedstuffs, ed. Applewhite (American Oil Chemists Society, Champaign, Illinois), pp. 497-502; herein incorporated by reference); corn (Pedersen, et al., (1986) J. Biol. Chem. 261:6279; Kirihara, et al., (1988) Gene 71:359; both of which are herein incorporated by reference); and rice (Musumura, et al., (1989) Plant Mol. Biol. 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) Gene 48:109); and the like.

Genes encoding disease resistance traits include detoxification genes, such as against fumonosin (U.S. Pat. No. 5,792,931); avirulence (avr) and disease resistance (R) genes (Jones, et al., (1994) Science 266:789; Martin, et al., (1993) Science 262:1432; and Mindrinos, et al., (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Genome Editing and Induced Mutagenesis

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein is generated using "custom" meganucleases produced to modify plant genomes (see, e.g., WO 2009/114321; Gao, et al., (2010) Plant Journal 1:176-187). Other site-directed engineering is through the use of zinc finger domain recognition coupled with the restriction properties of restriction enzyme. See, e.g., Urnov, et al., (2010) Nat Rev Genet. 11(9):636-46; Shukla, et al., (2009) Nature 459(7245):437-41.

"TILLING" or "Targeting Induced Local Lesions IN Genomics" refers to a mutagenesis technology useful to generate and/or identify and to eventually isolate mutagenised variants of a particular nucleic acid with modulated expression and/or activity (McCallum, et al., (2000), Plant Physiology 123:439-442; McCallum, et al., (2000) Nature Biotechnology 18:455-457 and Colbert, et al., (2001) Plant Physiology 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

TILLING also allows selection of plants carrying mutant variants. These mutant variants may exhibit modified expression, either in strength or in location or in timing (if the mutations affect the promoter, for example). These mutant variants may exhibit higher or lower activity than that exhibited by the gene in its natural form. TILLING combines high-density mutagenesis with high-throughput screening methods. The steps typically followed in TILLING are: (a) EMS mutagenesis (Redei and Koncz, (1992) In Methods in *Arabidopsis* Research, Koncz, et al., eds. Singapore, World Scientific Publishing Co, pp. 16-82; Feldmann, et al., (1994) In *Arabidopsis*. Meyerowitz and Somerville, eds, Cold Spring Harbor Laboratory Press, Cold Spring Harbor, N.Y., pp 137-172; Lightner and Caspar, (1998) In Methods on Molecular Biology 82:91-104; Martinez-Zapater and Salinas, eds, Humana Press, Totowa, N.J.); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (U.S. Pat. No. 8,071,840).

Other mutagenic methods can also be employed to introduce mutations in a disclosed gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Embodiments of the disclosure reflect the determination that the genotype of an organism can be modified to contain dominant suppressor alleles or transgene constructs that suppress (i.e., reduce, but not ablate) the activity of a gene, wherein the phenotype of the organism is not substantially affected.

Hybrid seed production requires elimination or inactivation of pollen produced by the female parent. Incomplete removal or inactivation of the pollen provides the potential for selfing, raising the risk that inadvertently self-pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor relative to the hybrid plants. For example, female selfed plants of e are identified by their less vigorous appearance for vegetative and/or reproductive characteristics, including shorter plant height, small ear size, ear and kernel shape, cob color or other characteristics. Selfed lines also can be identified using molecular marker analyses (see, e.g., Smith and Wych, (1995) Seed Sci. Technol. 14:1-8). Using such methods, the homozygosity of the self-pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. The present disclosure contributes to this goal, for example by providing plants that, when crossed, generate male sterile progeny, which can be used as female parental plants for generating hybrid plants.

A large number of genes have been identified as being tassel preferred in their expression pattern using traditional methods and more recent high-throughput methods. The correlation of function of these genes with important biochemical or developmental processes that ultimately lead to functional pollen is arduous when approaches are limited to classical forward or reverse genetic mutational analysis. As disclosed herein, suppression approaches provide an alternative rapid means to identify genes that are directly related to pollen development.

Promoters useful for expressing a nucleic acid molecule of interest can be any of a range of naturally-occurring promoters known to be operative in plants or animals, as desired. Promoters that direct expression in cells of male or female reproductive organs of a plant are useful for generating a transgenic plant or breeding pair of plants of the disclosure. The promoters useful in the present disclosure can include constitutive promoters, which generally are active in most or all tissues of a plant; inducible promoters, which generally are inactive or exhibit a low basal level of expression and can be induced to a relatively high activity upon contact of cells with an appropriate inducing agent; tissue-specific (or tissue-preferred) promoters, which generally are expressed in only one or a few particular cell types (e.g., plant anther cells) and developmental- or stage-specific promoters, which are active only during a defined period during the growth or development of a plant. Often promoters can be modified, if necessary, to vary the expression level. Certain embodiments comprise promoters exogenous to the species being manipulated. For example, the Ms45 gene introduced into ms45ms45 maize germplasm may be driven by a promoter isolated from another plant species; a hairpin construct may then be designed to target the exogenous plant promoter, reducing the possibility of hairpin interaction with non-target, endogenous promoters.

Exemplary constitutive promoters include the 35S cauliflower mosaic virus (CaMV) promoter (Odell, et al., (1985) Nature 313:810-812), the maize ubiquitin promoter (Christensen, et al., (1989) Plant Mol. Biol. 12:619-632 and Christensen, et al., (1992) Plant Mol. Biol. 18:675-689); the core promoter of the Rsyn7 promoter and other constitutive promoters disclosed in WO 1999/43838 and U.S. Pat. No. 6,072,050; rice actin (McElroy, et al., (1990) Plant Cell 2:163-171); pEMU (Last, et al., (1991) Theor. Appl. Genet. 81:581-588); MAS (Velten, et al., (1984) EMBO J. 3:2723-2730); ALS promoter (U.S. Pat. No. 5,659,026); rice actin promoter (U.S. Pat. No. 5,641,876; WO 2000/70067), maize histone promoter (Brignon, et al., (1993) Plant Mol Bio 22(6):1007-1015; Rasco-Gaunt, et al., (2003) Plant Cell Rep. 21(6):569-576) and the like. Other constitutive promoters include, for example, those described in U.S. Pat. Nos. 5,608,144 and 6,177,611 and PCT Publication Number WO 2003/102198.

Tissue-specific, tissue-preferred or stage-specific regulatory elements further include, for example, the AGL8/FRUITFULL regulatory element, which is activated upon floral induction (Hempel, et al., (1997) Development 124:3845-3853); root-specific regulatory elements such as the regulatory elements from the RCP1 gene and the LRP1 gene (Tsugeki and Fedoroff, (1999) Proc. Natl. Acad., USA 96:12941-12946; Smith and Fedoroff, (1995) Plant Cell 7:735-745); flower-specific regulatory elements such as the regulatory elements from the LEAFY gene and the APETALA1 gene (Blazquez, et al., (1997) Development 124:3835-3844; Hempel, et al., supra, 1997); seed-specific regulatory elements such as the regulatory element from the oleosin gene (Plant, et al., (1994) Plant Mol. Biol. 25:193-205) and dehiscence zone specific regulatory element. Additional tissue-specific or stage-specific regulatory elements include the Zn13 promoter, which is a pollen-specific promoter (Hamilton, et al., (1992) Plant Mol. Biol. 18:211-218); the UNUSUAL FLORAL ORGANS (UFO) promoter, which is active in apical shoot meristem; the promoter active in shoot meristems (Atanassova, et al., (1992) Plant J. 2:291), the cdc2 promoter and cyc07 promoter (see, for example, Ito, et al., (1994) Plant Mol. Biol. 24:863-878; Martinez, et al., (1992) Proc. Natl. Acad. Sci., USA 89:7360); the meristematic-preferred meri-5 and H3 promoters (Medford, et al., (1991) Plant Cell 3:359; Terada, et al., (1993) Plant J. 3:241); meristematic and phloem-preferred promoters of Myb-related genes in barley (Wissenbach, et al., (1993) Plant J. 4:411); *Arabidopsis* cyc3aAt and cyc1At (Shaul, et al., (1996) Proc. Natl. Acad. Sci. 93:4868-4872); *C. roseus* cyclins CYS and CYM (Ito, et al., (1997) Plant J. 11:983-992); and *Nicotiana* CyclinB1 (Trehin, et al., (1997) Plant Mol. Biol. 35:667-672); the promoter of the *APETALA*3 gene, which is active in floral meristems (Jack, et al., (1994) Cell 76:703; Hempel, et al., supra, 1997); a promoter of an agamous-like (AGL) family member, for example, AGL8, which is active in shoot meristem upon the transition to flowering (Hempel, et al., supra, 1997); floral abscission zone promoters; L1-specific promoters; the ripening-enhanced tomato polygalacturonase promoter (Nicholass, et al., (1995) Plant Mol. Biol. 28:423-435), the E8 promoter (Deikman, et al., (1992) Plant Physiol. 100:2013-2017) and the fruit-specific 2A1 promoter, U2 and U5 snRNA promoters from maize, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD zein protein, and the like. Additional tissue-specific promoters can be isolated using well known methods (see, e.g., U.S. Pat. No. 5,589,379). Shoot-preferred promoters include shoot meristem-preferred promoters such as promoters disclosed in Weigel, et al., (1992) Cell 69:843-859.

Use in Breeding Methods

The plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity and plant and ear height is desirable. Traditional plant breeding is an important tool in developing new and improved commercial crops. This disclosure encompasses methods for producing a plant by crossing a first parent plant with a second parent plant wherein one or both of the parent plants is a plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed plant to an elite inbred line and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1

As part of a study on inducibility a total of 102 public and expired Plant Variety Protection (ExPVP) inbred lines were pollinated with the maternal haploid inducer 'RWS/RWK-76' (Rober et al., 2005). Haploid kernels from these inbred lines were grown at the Iowa State University Agricultural Engineering and Agronomy Farm (ISU-AEA) in Boone, IA in a preliminary screening experiment. Twenty-five putative haploid kernels from each entry were directly planted with a plot planter in a two replication randomized complete block design. Observations of fertile male tassels with healthy anthers dehiscing at ISU-AEA along with discussions with users of the ISU DH Facility led us to the conclusion that male fertility limits successful self-fertilization of haploids, consistent with earlier reports. As consequence, we scored for haploid male fertility (HMF) in this germplasm. Three inbreds with superior (>50%) HMF were identified. Each of these inbred lines produced fertile anthers, successful self-pollinations and crosses onto other haploids. The three identified inbreds and their corresponding haploids were grown side-by-side for confirmation at ISU-AEA and the haploids consistently produced fertile anthers and were phenotypically distinct from their inbred counterpart. Additionally, a cross made between a HMF haploid from the highest doubling line and another non-doubling line was grown in the greenhouse at ISU producing fertile F1 plants which were induced with 'RWS/RWK-76'. These haploids were directly planted in the field and segregated for HMF at a near 1:1 ratio, confirming our observations that this is a heritable, stable, and selectable trait.

Three public inbred lines GF1, GF2, and GF6 were found to show HMF and thus, more generally, SHGD ability as haploids. In conjunction with another study, a six parent full diallel between these three SHGD lines and three non-SHGD lines was created and HMF in haploids was scored (De la Fuente, 2015). Diallel analysis showed that significant GCA estimates of up to 17% exist for SHGD as well as significant SHGD effects of up to 25%. There were no significant reciprocal effects observed, and broad and narrow sense heritabilities for SHGD estimates were at 0.62 and 0.31, respectively.

Maize inbred lines GF1 (with high HMF) and GF3 (with moderate HMF) were selected to develop mapping populations. HMF was determined for 1078 haploids of the GF1× GF3 (genotype with moderate HMF) population. The 45 fertile haploids with highest HMF and 30 random male sterile haploids were selected for further characterization.

We focused on anther emergence to determine SHGD. Anther emergence was visually scored on a scale of 0 (no anthers emerged, sterile) to 5 (more than 75% anthers emerged on the tassel). Those 75 haploids were genotyped with a 6K SNP chip, resulting in 2,032 polymorphic SNP markers (Ren et al. 2017). Segregation distortion was examined in selected fractions of the GF1×GF3 population using a $\chi 2$ test for goodness of fit to an expected segregation ratio of 1:1 of GF1 to GF3 alleles. More than 90% of GF1 haploids showed anther emergence and most of them showed high male fertility. About 70% of GF3 showed anther emergence and most of them only exhibited few anthers emerged on a tassel. The haploids from the respective F1 were evaluated for male fertility. About 70% haploids showed variable levels of haploid male fertility. On average, 51.5% of the marker are of GF1 alleles and 48.5% of the markers are of GF3 alleles. Nine chromosome regions showed significant segregation distortion (P=0.05) on chromosomes 1, 2, 3, 5, 6, 8, and 9, respectively, within either the fraction of fertile or sterile haploids, respectively. When looking at all haploids jointly, only the regions on chromosome 5.04 and 6-6.01 consistently showed significant segregation distortion.

Example 2

The chromosomal region 5.04 of maize contains the gene GRMZM2G009913. GRMZM2G009913 shows sequence homology to the *Arabidopsis* gene AT2G33560.2, annotated as (BUBR1) BUB1-related (BUB1: budding uninhibited by benzymidazol 1), and to the rice gene LOC Os02g10020.1, annotated as MAD3/BUB1 homology region 1 domain containing protein expressed. BUB1 and BUBR1 (also called MAD3—mitotic arrest deficient) are part of a spindle assembly checkpoint (SAC), a highly conserved control system in Eukaryotes, which ensures that the chromosomes are properly arranged on the mitotic spindle before the start of Anaphase (Bolanos-Garcia and Blundell, 2011).

The major difference between the non-doubler (B73) allele and the SHGD (GF1) allele is an amino acid change (Aspartic acid→Valine) in the MAD-BUB1 domain. A similar exchange could only be found in *Hordeum vulgare*, when comparing several representatives of the Poaceae (FIG. 3). Genomic DNA Sequences of the SHGD Allele (GF1) and a Non-Doubling Allele (B73)

```
GF1 SHGD Genomic Region (SEQ ID NO: 1):
CTTTAACAACCACTCTATATTTTGATCTATCTCTTTTATAAGTTTGAGTTCATGTGACTTATTTTAGAAACTT

GAGCTTACAAACTTTCTCTTATTTGGTCTCTGTATAGCGGAATTATGTCATTCTATAATCTATGTTCGTTCAG

TCAGTCGTTATGAACTCTCTTATAGTCGCTCATTTCATTGGTTGTGTTGTACCAAGACATATTGGATGGAGTA

AACAATAACATCAGTTAGCCAAATCAAAATAACATTATACGGAGAGCAGAGACAAATAATAAAAAATCTTGAT

ATTTTTTATGGATTTACGTGGGTATTGTTGTAAGCCGTCGTAACGCACGGGTAACCGACTAGTATTAGTAATA

ATTGAGTTATATCTATGAATTTTAAGCCTTCTCACGTTGAGCGCAACAAAATATTTAATGAATAATTAGCCAA

CCTACTTATTCAAAAATAATTACTATTGTATTGTATCATAAGTAGTATTGTGCAAATTAAAGAATGATCCAAA

TTTTGTGTCGGGTGTGGGTCACCAATGGGTTGAAGTAGAAACCTGCATAACACTCGTGAAACTTTGAGTCGAG

TGTGGGGTGCACTCACGGGTTAAAATTTTTACCTGTACCCGCACCCGTCGGGTTGGGTACGTGTCGAGTTTTG

GGTTTGCGGGTTAAATTGCCATCCCTACATAAAAGTGTAGAGGGGAGGAAAGACATGAGTGTGCTCACATCCG

ATCGTTTTGATGAAGTAGAGACATCTCAATTATTTATGATATATTTTCATACGGAGACTATAGGAGTCGCTTT

ACTCTCTTTCATTAGAAACCAAACATCTAAAAAAAATAGAACTGGATTGGTTCCATTCGCATCCACTCTTTTA
```

-continued

```
CCAAACACATCCTAATATATGTACTTGGTGGAGTAATTTAGTCCTCGTTTCATGGTTGCTTTTTTTGCTAAA
ATTTACGCTTCTCATGGCATACAGCCAGTTGAATTTGTTCCAGCCAAGCAAAACATAGCTGGGCTATTTGAG
TACAAACCGGCCCAAATAAAACATGGGAGTAACTAAAAGCCTACGGCCCAAACTTTTCGCAAAGCTTCACCGT
TTAAAACCGAAACCTGACCTGCGGGCTGCAGCAGCGTCCGCTCCAAAACGCAACGGTCGAATCTCCTCGAATT
CGAATTGCAGCCGGTGCCACCCACCTCACATGGCGGCGGCGGAAGAGATGATGGCGGTGCTGGACAAGGAGAC
GCTGGCGCTGATGGGTCTGGGCAACGCCGCCGCCGCGGTGGTTGTCGAGTGCGAGAAGTTCAAGGAGAACGCG
AGGCCGCTCAAGCGCGGGCGCGACGTGTCCAAACTCAACCACGCGCTCAAGGCACACGCCGATCCCGCCCAGC
GCGCCACTCTTCTCGAAGCCCGAAAGTACGTTTCCTTCTCCAGTCTTTCGCCCAGCAATGGGGGAGAAAGAGT
TGTGGTTTTGTAACTTTTGTTTGCTCTGGATTTCTTTTTCTTGGGCCTGGGTCTCTGGGGAGGAGACAAGTTG
CTGCAGTAATGCAAATATATATCATGTGTGTTCATCGTTCGGTTCATTTGCTTGATCCAGGAAGATGATTGAG
GCAATCTACGAGTACCAAGGCGAGGATCCGCTCCAACCGTGGCTGGAGTAAGTTTTTCTCGAAGCCCCTTTAA
CTCGCCTTTTTCGATTTCTTGGTTCGTGCCAGGACTGGTAGCTGTTCTAGCAGATAGATTGTTCATTTCTTC
TCTGATTCGTCCGCGTGCAGCTGCATCAAGTGGGTGCAGGAGTATTTTCCGACCGGCGGCGAGTGCTCAGGGT
TGGTGGTGTTGTACGAGCAGTGCGTGCGGACCTTATTGGATGACGAGCGCTACAAGGACGACCTCCGCTTCCT
CAAAGTGTGGCTGGAATACGTGAGTGATGCTTTGCCAGCTTGATTGTTTTTCTCTGTAGTTTGTGTCAGTGCA
GTGAAGGCACCTCATATATCATTCCGCTGCCGATCTTGTCCTTTTTGCAGGCGGGGAACTGTGCTGATGCTGA
GGTAATATACAGGTTCCTGGAGGCCAACCAGATTGGGCAGGGCCATGCGATCTACTACATGTCTTACGCATCG
TTGATGGAGTCAAAGAACAAGTTGAGGAAAGCTAATGAGATCTTTGTCCTTGGTATAGCTAGGTGAGATTTTC
TTTAGATCAGCACGTTTGTTCATATAAAGCTCCTGAGTTTTAAATTGTTCGGTAGATCATGCTGTTGTACTAT
ATATCCGATCCAAAAATTGTGTCCTATAATGGACATGGAGTGGGTACATATATGCTCCTGTGTTTGATTTTCG
TACATAACAAGAGTCAATGATGGTACAAAAATGAGGCTGATGTTATACTGAATCAGTTTTCCTTCTTTGTTTT
ATTTCCATGATCACTTCTAATTTGATACATGCTAACGAATTAGAAATAAAAAGTTCCTTTTAGTTTCTAGTTT
GCAAACGTAAATGAAAAAAAAATCTTAGTCTTCTACTTCCTATTCTTTAAGATTTGACACTCCTTTGACTAG
TTATGCCACTATCTTCTTGTAAATGATAAACACTCGGAATTGTTTTACTTATCATGGTTTCTGCTTACCTCTT
TTGTTATGGTTAGTTGTGCATTGGTTTTAATACTTGATTAATCCATGTGAATGTATGAAGTTTCTTATATTCG
ATTTTTTATTGTCAGAAAAGCGAAGCCTCTGGAGAAGTTGGAAGCTGTATACAGGGCATTTCTTCGAAGATCA
ATCAAAAAGAGGGAACAAGAGGTTTGCTATTTAAATTACAGCAGTGTTTATTTATCTTGAAGCCAATACCTCA
GTTGAATGACTTCTTTCTTTTCCTGTAGCAGGATGATACAGTAGATGATGATCTGCCAAAACGCAGTTTCGGG
AATAACTTGAAACGAGATGAAAACAGTAAGCTTGTTCAGTTTTACTCTGATTAGCATGAACTTCGAGTGGCT
GCAACCTAATACATATGCAAACATGGCAGGAAATCAGCAAGCAGGGAACTCCCACCTGGGGAGACCAAGGGCA
CTGCAGAGGTCAGTACCTGTATGATGTGACAGATGTAAAATTTCCATCTAAACCTGGAGTTTGTTTTTTCTCA
TCAAGTCACTGATTATGCCTTTGCACACTTGCGGAATCGATGCTAACAGGCCGCTTTCAGTTTACAAAGATGA
AAGTCCATTACCAAATCAGGGCCTTGACAGAGTGAGGAGCAAAGAAAATAACACAAGTTGGCGCACCCTCGGA
ACACGAGCAGAACGGAACAAGGAAAATAACATGATGCCTGCTAAATGGACGTCTCACAAGGTACGTTTGCCAT
GCCATTTAGGATTCTCTGAAGTGGCCCATGTGAGACTTGCACCGAGGACAACTATTCAGTAACGAACTTGTTG
TACAGATCCCACAGAAGTTAGGAGCAAGAGGAGCGGTTCAATCAACCCGAGCCAGTTGTTCCATTGAAGTCTT
CGTCGAGGAAGACTGCACACAGTATGTTATTTAACATGCTAGTGTTACTCTTTTTTTTTGAGATTGTTCAAA
GTTACTACAAAAACATATATGTCTAAATAGACTCTTTTTCCCTTTGGATTGCTGTAGTGAACCTGCTCGGCCG
GTGCCAAAGAGCCCAAATCCTTCTGTTCTGAAGCTCAGGCAAACAACAAGCAAAAGCCTTAAGAAGTAAGTAC
AGCATAGCTCTTGTAGCTTCGGGTATTTGGGAAACTATTGTCAGCAGTTCCCTAACCTCTGCGGTCTTTTCTT
TGGAGCAGGGAGACTGAATTGCTCAAGGAGAACCCGCTGCGCAACTTCCCCCTGAGCAGGCTTAGGTAATCAG
```

-continued

```
CATCTTGCTGGTTCTGAGAAACATCTCGTACGTTATGATTTGGTCGTATGTATGGTTGCTGTGAGGTGTTGTG

CCCAAAAAAAGGCTTTATTAGCCTCTAAAGCTTAGACGAGCAATGTATGCCTATGGCATTACCCAAGTGCTG

TAAGGTTCTGCATTATATTGACACGGCGTGCTTATTATTGATAGACCTGCAGATCTCGTGCGTGCCTATGTGT

ATCTAATAGCCTCGCAAATAATCTGCTTCTGCAAATTCTAATAGCTTGTTCTGTAATGAAAATGCCTTTGGA

CTAATATCTAATAGCGTCTCGTTCCTTGCATGTGAATCCCGCGGCCATGGCGGCCGGAG
```

B73 Reference Genomic Region (SEQ ID NO: 2):
```
GATCTATCTTTTTTATAAGTTTGAGTTCATGTGACTTATTTTAGAAACTTGAGCTTACAAACTTTCTCTTATT

TGGTCTCTGTATATAGGAATTATGTCATTCTATAATCTATGTTCGTTCAGTCAGTCGTTATGAACTCTCTTAT

AATCGCTCATTTCATTGGTTGTGTTGTACCAAGACATACTGGATGGAGTAAACAATAACATCAGTTAGCCAAA

TCAAAAAAACATTATACGGAGAGCAGAGACAAATAATAAAAAATCTTGATATTTTTATGGATTTACGTGGGTA

TTGTTGTAAGCCGTCGCAACGCACGGGTAACCGACTAGTATTAGTAATAATTGAGTTATATCTATGAATTTTA

AGCCTTCTCACGTTGAGCGCAACAAAATATTTAATGAATAATTAGCCAACCTACTTATTCAAAAATAATTACT

ATTGTATTGTATCATAAGTAGTATTGTGCAAATTAAAGAATGATCCAAATTTTGTGTCGGGTGTGGGTCACCC

ATGGTTGAAATAGAAACCTGCATAACACTCGTGAAACTTTGAGTCGAGTCTGGGGTGCACTCACGGGTTAAAA

TTTTTACCTGTACCCGCACCCGTCGGGTTGGGTACGTGTCGAGTTTCGGGTTTGCGGGTTAAATTGCCATCCC

TACATAAAAGTGTAGGGGGGAGGAAAGACATGAGTATGCTCACATCCGATCGTTTTGATGGAGCAGAGACATC

TCAATTATTTATGATATATTTTTATACGGAGACTATAAGAGTCGCTTTACTCTCTTTCATTAGAAACCAAACA

TCTACAAAAAATAGAACTGGATTGGTTCCATTCGCATCCACTCTTTTACCAAACACATCCTAATATATGTACT

TGGTGGAGTAATTTAGTCCTCGTTTCATGGTTGCTTTTTTTTTTTTGCTAAAATTTACGCTTCTCATGGCA

TACAGCCAGTTGAATTTGTTCCAGCCAAGCAAAACATAGCTGGGCTATTTTGAGTACAAACCGGCCCAAATAA

AACATGGGATTAACTAAAAGCCTACGGCCCAAACTTTTCGCAAAGCTTCACCGTTTAAAACCGAAACCTGACC

TGCGGGCTGCAGCAGCGTCCGCTCCAAAACGCAACGGTCGAATCTCCTCGAATTCGAATTGCAGCCGGTGCCA

CCCACCTCACATGGCGGCGGCGGAAGAGATGATGGCGGTGCTGGACAAGGAGACGCTGGCGCTGATGGGTCTG

GGCAACGCCGCCGCCGCGGTGGTTGCCGAGTGCGAGAAGTTCAAGGAGAACGCGAGGCCGCTCAAGCGCGGGC

GCGACGTGTCCAAACTCAACCACGCGCTCAAGGCACACGCCGATCCCGCCCAGCGCGCCACTCTTCTCGAAGC

CCGAAAGTACGTTTCCTTCTCCAGTCTTTCGCCCAGCAATGGGGGAAAAGGAGTTGTGGTTTTGTAACTTTTG

TTTGCTCTGGATTTCTTTTTCTTGGGCCTGGGTCTGTGGGGAGGAGACAAGTTGCTGCAGTAATGCAAATATA

TATCATGTGTGTTCATCGTTCGGTTCATTTGCTTGATCCAGGAAGCTGATTGAGGCAATCTACGAGTACCAAG

GCGAGGATCCGCTCCAACCGTGGCTGGAGTAAGTTTTTCTCATAGCCCCTTTAACTCGCCTTTTTCGATTTCT

TGGTTCGTGCCAGGACTGGTAGCTGTTCTAGCAGATAGATTGTTCATTTCTTCTCTGATTCGTCCGCGTGCAG

CTGCATCAAGTGGGTGCAGGAGTATTTTCCGACCGGCGGCGAGTGCTCAGGGTTGGTGGTGTTGTACGAGCAG

TGCGTGCGGACCTTATTGGACGACGAGCGCTACAAGGACGACCTCCGCTTCCTCAAAGTGTGGCTGGAATACG

TGAGTGATGCTTTGCCAGCTTGATTGTTTTTCTCTGTAGTTTGTGTCAGTGCAGTGGAGGCACCTCATATATC

ATTCCGCTGCCGATCTTGTCCTTTTTGCAGGCGGGGAACTGTGCTGATGCTGAGGTAATATACAGGTTCCTGG

AGGCCAACCAGATTGGGCAGGGCCATGCGATCTACTACATGTCTTACGCATCGTTGCTGGAGTCAAAGAACAA

GTTGAGGAAAGCTAATGAGATCTTTGACCTTGGTATAGCTAGGTGAGATTTTCTTTAGATCAGCACGTTTGTT

CATATAAAGCTCCTGAGTTTTAAATTGTTAGGTAGATCATGCTGTTGTACTATATATCCGATCCAAAAATTGT

GTCCTATAATGGACATGGAGTACATATATGCTCCTGTGTTTGATTTTCGTACATAACAAGAGTCAATGATGGT

ACAAAAATGAGGCTGATGTTATACTGAATCAGTTTTCCTTCTTTGTTTTATTTTCATGATCACTTCTAATTTG

ATACATTCTAACGAATTAGAAATAAAAAGTTCCTTTTAGTTTCTAGTTCGCAAACGTAAAATGAAAAAAAAT

CTCAGTCTTCTACTTCCTATTCTTTAAGATTTGACACTCCTTTGACTAGTTATGCCACTATCTTCTTGTAAAT
```

```
GATACAACACTCGGAATTGTTTTACTTATCATGGTTTCTGCTTACCTCTTTTGTTATGGTTAGTTGTGCATTG
GTTTTAATACTTGATTAATCCATGTGAATGTATGAAGTTTCTTATATTCGATTTTTTATTGTCAGAAAAGCGA
AGCCTCTGGAGAAGTTGGAAGCTGTATACAGGGCATTTCTTCGAAGATCAATCAAAAAGAGGGAACAAGAGGT
TTGCTATTCAAATTACAGCAGTGTTTATTTATCTTGAAGCCAATACCTCAGTTGAATGACTTCTTTCTTTTCC
TGTAGCAGGATGATACAGTAGATGATGATCTGCCAAAACGCAGTTTCGGGAATAACTTGAAACGAGATGAAAA
CAGTAAGCTTGTTCAGTTTTACTCTGATTTAGCATGAACTTCGAGTGGCTGCAACCTAATACATATGCAAACA
TGGCAGGAAATCAGCAAGCAGGGAACTCCCACCTGGGGAGACCAAGGGCACTGCAGAGGTCAGTACCTGTATG
ATGTGACAGATGTAAAATATCCATCTAAACCTGGAGTTTTTTTTCCTCATCATGTCACTGATTATGCCTTTGC
ACACTTGCGGAATCGATGCTAACAGGCCGCTTTCAGTTTACAAAGATGAAAGTCCATTACCAAATCAGGGCCT
TGACAGAGTGAGGAGCAAAGAAAATAACACAAGTTGGCGCGTCCTCGGAACACGAGCAGAACGGAACAAGGAA
AATAACATGATGCCTGCTAAATGGACGTCTCACAAGGTACTTTTGCCATGCCATTTAGGATTCTCTGAAGTGG
CCCATGTGAGACTTGCACCGAGGACAACTATTCAGTAACGAACTTGTGGTAACACTGCATTGTTGTTGTACAG
ATTCCACAGAAGTTAGGAGCAAGAGGAGCGGTTCAATCAACCCGAGCCAGTTGTTCCATTGAAGTCTTCGTCG
AGGAAGACTGCACACAGTATGTTATTTAACATGCTAGTGTTACTCTTTTCTTTTTTGAGATTGTTCAAAGTTA
CTACAAAAACATATATGTCTAAATAGACTCTTTTTTTCCCCTTTGGATTGCTGTAGGGAACCTGCTCGGCCGG
TGCCAAAGAGCCCAAATCCTTCTGTTCTGAAGCTCAGGCAAACAACAAGCAAAAGCCTTAAGAAGTAAGTACA
GCATAGCTCTTGTAGCTTCGGGTATTTGGGAAACTATTGTCAGCAGTTCCCTAACCTCTGCGGTCTTTTCTTT
GGAGCAGGGAGACTGAATTGCTCAAGGAGAACCCGCTGCGCAACTTCCCCCTGAGCAGGCTTAGGTAATCAGC
ATCTTGCTGGTTCTGAGAAACATCTCGTACGTTATGATTTGGTCGTATGTATGGTTGCTGTGAGGTGTTGTGC
CCAAAAAAGGCTTTATTAGCCTCTAAAGCTTAGACGAGCAATGTATGCCTATGGCATTATCCAAGTGATGTAA
GGCTGTGCATTATATTGACACGGCGTGCTTATTATGAATAGACCTGCAGATCTCGTGCGTGCCTATGTGAATC
TAGCCTCGCAAAATAATCTGCTTCTGCAAATTCTAATAGCTTGTTCTGTAACGAAAATGCCTTTGGACTAATA
TCTAATAGCGTCTCATTCAGTTTGTTTATATTTGAATGCCTGAGAAATTAGAAAACATATTTGAATGTTTTAT
TCCGTCCATAAATATAGAATCTCTGTAAGCATGTAGCTAAACTCAATAGAAACAT
```

Sequences of the SHGD protein (GF1) and a non-doubling protein (B73). The region of the MAD/BUB1 domain is in bold. The D239V amino acid change is underlined.

GF1 SHGD Protein Sequence (SEQ ID NO: 3):
MGVTKSLRPKLFAKLHRLKPKPDLRAAAASAPKRNGRISSNSNCSRCHPP
HMAAAEEMMAVLDKETLALMGLGNAAAAVVVECEKFKENARPLKRGRDVS
KLNHALKAHADPAQRATLLEARKKMIEAIYEYQGEDPLQPWLDCIKWVQE
YFPTGGECSGLVVLYEQCVRTLLDDERYKDDLRFLKVWLEYAGNCADAEV
IYRFLEANQIGQGHAIYYMSYASLMESKNKLRKANEIFV̲LGIARKAKPLE
KLEAVYRAFLRRSIKKREQEQDDTVDDDLPKRSFGNNLKRDENRNQQAGN
SHLGRPRALQRPLSVYKDESPLPNQGLDRVRSKENNTSWRTLGTRAERNK
ENNMMPAKWTSHKIPQKLGARGAVQSTRASCSIEVFVEEDCTHEPARPVP
KSPNPSVLKLRQTTSKSLKKETELLKENPLRNFPLSRLR B73 GRMZM2G009913_P01 Reference Protein Sequence (SEQ ID NO: 4):
MGLTKSLRPKLFAKLHRLKPKPDLRAAAASAPKRNGRISSNSNCSRCHPP
HMAAAEEMMAVLDKETLALMGLGNAAAAVVAECEKFKENARPLKRGRDVS
KLNHALKAHADPAQRATLLEARKKLIEAIYEYQGEDPLQPWLDCIKWVQE
YFPTGGECSGLVVLYEQCVRTLLDDERYKDDLRFLKVWLEYAGNCADAEV
IYRFLEANQIGQGHAIYYMSYASLLESKNKLRKANEIFD̲LGIARKAKPLE
KLEAVYRAFLRRSIKKREQEQDDTVDDDLPKRSFGNNLKRDENRNQQAGN
SHLGRPRALQRPLSVYKDESPLPNQGLDRVRSKENNTSWRVLGTRAERNK
ENNMMPAKWTSHKIPQKLGARGAVQSTRASCSIEVFVEEDCTQEPARPVP
KSPNPSVLKLRQTTSKSLKKETELLKENPLRNFPLSRLR cDNA Sequences of the SHGD Allele (GF1) and a Non-Doubling Allele (B73)

Gf1 SEEM cDNA Sequence (SEQ ID NO: 5):
ATGGGAGTAACTAAAAGCTACGGCCCAAACTTTTCGCAAAGCTTCACCG
TTTAAAACCGAAACCTGACCTGCGGGCTGCAGCAGCGTCCGCTCCAAAAC
GCAACGGTCGAATCTCCTCGAATTCGAATTGCAGCCGGTGCCACCCACCT
CACATGGCGGCGGCGGAAGAGATGATGGCGGTGCTGGACAAGGAGACGCT
GGCGCTGATGGGTCTGGGCAACGCCGCCGCCGCGGTGGTTGTCGAGTGCG

```
AGAAGTTCAAGGAGAACGCGAGGCCGCTCAAGCGCGGGCGCGACGTGTCC
AAACTCAACCACGCGCTCAAGGCACACGCCGATCCCGCCCAGCGCGCCAC
TCTTCTCGAAGCCCGAAAGAAGATGATTGAGGCAATCTACGAGTACCAAG
GCGAGGATCCGCTCCAACCGTGGCTGGACTGCATCAAGTGGGTGCAGGAG
TATTTTCCGACCGGCGGCGAGTGCTCAGGGTTGGTGGTGTTGTACGAGCA
GTGCGTGCGGACCTTATTGGATGACGAGCGCTACAAGGACGACCTCCGCT
TCCTCAAAGTGTGGCTGGAATACGCGGGGAACTGTGCTGATGCTGAGGTA
ATATACAGGTTCCTGGAGGCCAACCAGATTGGGCAGGGCCATGCGATCTA
CTACATGTCTTACGCATCGTTGATGGAGTCAAAGAACAAGTTGAGGAAAG
CTAATGAGATCTTTGTCCTTGGTATAGCTAGAAAAGCGAAGCCTCTGGAG
AAGTTGGAAGCTGTATACAGGGCATTTCTTCGAAGATCAATCAAAAAGAG
GGAACAAGAGCAGGATGATACAGTAGATGATGATCTGCCAAAACGCAGTT
TCGGGAATAACTTGAAACGAGATGAAAACAGAAATCAGCAAGCAGGGAAC
TCCCACCTGGGGAGACCAAGGGCACTGCAGAGGCCGCTTTCAGTTTACAA
AGATGAAAGTCCATTACCAAATCAGGGCCTTGACAGAGTGAGGAGCAAAG
AAAATAACACAAGTTGGCGCACCCTCGGAACACGAGCAGAACGGAACAAG
GAAAATAACATGATGCCTGCTAAATGGACGTCTCACAAGATCCCACAGAA
GTTAGGAGCAAGAGGAGCGGTTCAATCAACCCGAGCCAGTTGTTCCATTG
AAGTCTTCGTCGAGGAAGACTGCACACATGAACCTGCTCGGCCGGTGCCA
AAGAGCCCAAATCCTTCTGTTCTGAAGCTCAGGCAAACAACAAGCAAAAG
CCTTAAGAAGGAGACTGAATTGCTCAAGGAGAACCCGCTGCGCAACTTCC
CCCTGAGCAGGCTTAGGTAA
B73 Reference cDNA Sequence (SEQ ID NO: 6):
ATGGGATTAACTAAAAGCCTACGGCCCAAACTTTTCGCAAAGCTTCACCG
TTTAAAACCGAAACCTGACCTGCGGGCTGCAGCAGCGTCCGCTCCAAAAC
GCAACGGTCGAATCTCCTCGAATTCGAATTGCAGCCGGTGCCACCCACCT
CACATGGCGGCGGCGGAAGAGATGATGGCGGTGCTGGACAAGGAGACGCT
GGCGCTGATGGGTCTGGGCAACGCCGCCGCCGCGGTGGTTGCCGAGTGCG
AGAAGTTCAAGGAGAACGCGAGGCCGCTCAAGCGCGGGCGCGACGTGTCC
AAACTCAACCACGCGCTCAAGGCACACGCCGATCCCGCCCAGCGCGCCAC
TCTTCTCGAAGCCCGAAAGAAGCTGATTGAGGCAATCTACGAGTACCAAG
GCGAGGATCCGCTCCAACCGTGGCTGGACTGCATCAAGTGGGTGCAGGAG
TATTTTCCGACCGGCGGCGAGTGCTCAGGGTTGGTGGTGTTGTACGAGCA
GTGCGTGCGGACCTTATTGGACGACGAGCGCTACAAGGACGACCTCCGCT
TCCTCAAAGTGTGGCTGGAATACGCGGGGAACTGTGCTGATGCTGAGGTA
ATATACAGGTTCCTGGAGGCCAACCAGATTGGGCAGGGCCATGCGATCTA
CTACATGTCTTACGCATCGTTGCTGGAGTCAAAGAACAAGTTGAGGAAAG
CTAATGAGATCTTTGACCTTGGTATAGCTAGAAAAGCGAAGCCTCTGGAG
AAGTTGGAAGCTGTATACAGGGCATTTCTTCGAAGATCAATCAAAAAGAG
GGAACAAGAGCAGGATGATACAGTAGATGATGATCTGCCAAAACGCAGTT
TCGGGAATAACTTGAAACGAGATGAAAACAGAAATCAGCAAGCAGGGAAC
TCCCACCTGGGGAGACCAAGGGCACTGCAGAGGCCGCTTTCAGTTTACAA
AGATGAAAGTCCATTACCAAATCAGGGCCTTGACAGAGTGAGGAGCAAAG
AAAATAACACAAGTTGGCGCGTCCTCGGAACACGAGCAGAACGGAACAAG
GAAAATAACATGATGCCTGCTAAATGGACGTCTCACAAGATTCCACAGAA
GTTAGGAGCAAGAGGAGCGGTTCAATCAACCCGAGCCAGTTGTTCCATTG
AAGTCTTCGTCGAGGAAGACTGCACACAGGAACCTGCTCGGCCGGTGCCA
AAGAGCCCAAATCCTTCTGTTCTGAAGCTCAGGCAAACAACAAGCAAAAG
CCTTAAGAAGGAGACTGAATTGCTCAAGGAGAACCCGCTGCGCAACTTCC
CCCTGAGCAGGCTTAGGTAA
```

TABLE 1

| Gene specific PCR-marker. | |
|---|---|
| name | sequence (5'-3') |
| 913-1FW (SEQ ID NO: 18) | AGGATTCTCTGAAGTGGCCC |
| 913-1R (SEQ ID NO: 19) | CGCTCCTCTTGCTCCTAACT |

Product Size: 101

GF1 product is 19 bp shorter than B73. The forward primer is located in the intron between exon 8 and 9, the reverse primer is located in exon 9.

TABLE 2

| Flanking SSR marker. | | | | |
|---|---|---|---|---|
| name | sequence (5'-3') | position (B73 RefGen.v4) | SSR | expected product size in B73 |
| 504_21F (SEQ ID NO: 20) | AGAGCCGTCCGTCTGTATGTAA | 120453897 | (CATA)3 | 115 |
| 504_21R (SEQ ID NO: 21) | CCTTTCGCGTTTGCTTTGTA | 120454012 | | |
| p-umc2302F (SEQ ID NO: 22) | GCATATGCGAGATCATATCGTTGA | 130789398 | (TTTC)8 | 103 |
| p-umc2302R (SEQ ID NO: 23) | CTATACAGCCCTCAGCTCTGCTGT | 130789295 | | |

Example 3

As a first step toward transgenic validation of the BUBR1 gene, a full-length construct using the allele from GF1 was transformed into a transformable genotype (B104) at the plant transformation facility of ISU. Seven independent events were crossed with the haploid inducer, to produce haploid plants for those seven events. In total, 728 haploid plants were planted in the transgenic nursery along with additional non-transgenic haploid control plants carrying or not carrying the GF1 allele.

Across the seven tested events, there was no significant difference between haploids carrying or not carrying the transgenic GF1 allele of the BUBR1 gene with regard to the PP score (for fertile pollen production), which was below 5% in both cases. For comparison: non-transgenic (control) haploid plants carrying the GF1 chromosome region had a PP score of 35%. The observation of no impact on doubling by adding the full-length construct can be due to suppression by the allele present (due to dominant/recessive gene action) in the transformable genotype (B104).

Genome editing was used to co-transform two constructs: one targeting and destroying the endogenous B104 allele of BUBR1 by CRISPR, and the second adding the full length GF1 allele. Events with the B104 allele knocked out but complemented by the GF1 allele will eliminate suspected dominance relationships. In addition, knock-out events will show whether the effect of the GF1 allele on male fertility/SHGD is due to loss-of-function, rather than gain of function.

Example 4

Biparental QTL Mapping of Spontaneous Haploid Genome Doubling Using Genotype by Sequencing Approach in Maize To identify QTL controlling SHGD, a $F_{2:3}$ mapping population was developed from A427 and CR1Ht. Haploids from $F_{2:3}$ families were planted in three environments and scored for SHGD. A linkage map of 4,171 markers covering a genetic map length of 2,141 cM was used for QTL mapping. A total of 15 QTL were found all three traits evaluated on chromosomes 1, 5, 6, 7, and 10. A major QTL was found chromosome 5, corresponding to the region with BUBR1 (GRMZM2G009913), which showed pleiotropic effects for all three traits. It explained 51.32% for anther emergence (AE), 55.93% for pollen production (PP), and 48.48% for tassel size (TS).

Materials and Methods
Population Development

A biparental population of 218 F2:3 families were formed from a cross between A427 and CR1Ht. A427 is a public non-stiff stalk inbred line develop out of University of Minnesota (GRIN). CR1Ht is an exPVP non-stiff stalk inbred line develop by J.C. Robinson Seed Company. Both inbreds were A427 showed a high rate of haploid male fertility at 78% based on preliminary data (not shown). In contrast, CR1Ht showed a low rate of haploid male fertility at 22%. Iowa State High Inducers (BHI305, BHI306, BHI307, and BHI310) were bulked together due to limited seed to form maternal haploid inducer. The 218 $F_{2:3}$ families were planted as the donor in isolation and pollinated with Iowa State High Inducers. A representative sample of haploids from each family was bulked together to maximize variation within each family.

Experimental Design

Field trials were conducted in 2017 growing season at the Agricultural Engineering and Agronomy Farm (AEA) in Boone, IA (N 42° 01'14.4" W 93° 46'36.1") and Plant Introduction Station (PI) in Ames, Iowa (N 42° 00'38.5" W 93° 39'32.5"). The three environments AEA 2017 Early (AEAE) was planted on May 26, 2017, AEA 2017 Late (AEAL) was planted on Jun. 13, 2017, and PI 2017 (PI) was planted on May 16, 2017. The population of 218 F2:3 families with parents (A427 and CR1Ht) were evaluated in alpha lattice design in 15 incomplete blocks and each block contained 15 F2:3 families or parental check of A427 or CR1Ht. The trials were planted on 3.81 m plots and 0.76 m spacing. Hybrid plants (misclassified haploids) were remove from the field at the V4 growth stage based on visual appearance. Standard agronomic practices were used for all field trial locations.

Phenotypic Evaluation

Phenotyping was completed for anther emergence, pollen production, ear formation, tassel size on fertile haploids, pollination of haploid plant, pollen and silk presence at same time, total number of double haploid lines (DHL), and seed set on each DHL. Anther emergence was evaluated using a rating scale of 0-5. The rating scale follows rating scale from[1], which as follows 0 is sterile tassel with no anthers, and scales 1-5 are less 5%, 6-20%, 21-50%, 51-75%, 76-100%. Ear formation was evaluated as binary trait. Tassel size was evaluated on 1-5 scale. Scales of 1-5 are as follows central spike, central spike and 1 tassel branch, central spike and 2 or 3 tassel branches, central spike and 4 or 5 tassel branches, central spike with 6 or more tassel branches. Pollination of haploid was evaluated as binary trait. Pollen and silk presence at the time of pollination was evaluated as binary trait. Total number of DHLs was a count of number DHL containing one or more number of seed. Seed set on each DHL was total number of kernels on each ear. Haploids were score throughout the pollination season. The peak rating was used for the analysis.

Genotyping

Plant tissue was collected from 10 V2 maize plants from each F2:3 family and pooled together to form a sample to represent each F2 plant. DNA extraction and genotyping were conducted by Cornell Genomic Diversity Facility. DNA was digested with ApeKI restriction enzyme and DNA fragments from 384 individuals were pooled together for sequencing. Cornell Bioinformatics conducted the alignment to Maize B73 RefGen_v2 (www.maizegdb.org) and the calling of SNPs using the Tassel 5.0 GBS Production Pipeline[2].

GBS Correction

TASSEL software[3] was used to filter GBS Data. Filtering was performed across all sites and parameters were as follows: 25% missing data, minor allele frequency of 0.05, and major allele frequency of 0.95. A custom R script was created to filter each site for 2 alleles. TASSEL plugin GenostoABHPlugin converted the SNPs nucleotides to ABH format for genotype correction. Genotype-Corrector[4] was used for correction of heterozygous sites. A sliding window approach was used to correct the heterozygous sites. A window size of 25 SNPs was used for correction.

Linkage Map Construction

Binning of markers was conducted by using the BIN function within QTL IciMapping V4.1[5]. Chi square tests were used to identify SNPs with significant segregation distortion. Markers with a value of p<0.001 were deleted. The linkage map had a total length of 2141.2 cM. Linkage map contained 4,171 markers across 10 linkage groups with average distance between adjacent markers of 1.95 cM.

QTL Mapping

QTL mapping was conducted using QTL IciMapping v4.1[5]. The BIP functionality was used to evaluate QTL in single location. The MET functionality was used to evaluate QTL by environment interactions for multi-environment trials. LOD threshold was set of 1,000 permutation tests using Type I error at P<0.05.

Statistical Analysis

Field trials were analyzed both together and separately. An ordinal regression with proportional odd assumption was used to obtain BLUPs for each $F_{2:3}$ family. A mixed effects model was used to account for the unbalanced data due to false positive and emergence rates of haploid plants. The analysis was conducted using c/mm functionality from ordinal package[6] in R software version 3.5.0[7]. The model for field trials was:

$$Y_{jkl} \sim \text{Multinomial}(1, \pi_{ijkl})$$

$$\log\text{it}(\pi_{ijkl}) = \theta_i + R_j + B_{(j)k} + F_1$$

where $\theta_i$ is the intercept for the ith response category (i=0, 1, 2, 3, 4, 5), $R_j$ is the effect of the jth replication, $B_{(j)k}$ is the effect of the kth block nested in the jth replication.

explained considerable phenotypic variation across the environments; 32.52% at PI, 41.80% at AEAE, and 43.25% for AEAL.

For TS, a total of 8 QTL were identified in three environments. The detected QTL were dispersed over chromosomes 5, 6, 7, and 10. The phenotypic variance explained by additive effect QTL was 4.10% to 39.98%. The chromosome 5 region that was identified for anther emergence and pollen production was shown to be association with tassel size of male fertile haploids.

Most of QTL were small effect QTL, except for a pleiotropic QTL on chromosome 5, that appears to control anther emergence, pollen production, and tassel size.

QTL X Environment Analysis for AE, PP, and TS Traits

A total of 15 QTL were detected using QTL by environment analysis. Only one QTL, qTS6b, showed a strong QTL by environmental interaction. All other 14 QTLs showed a relatively minor QTL by environmental interaction. The chromosome 5 region was also found to be highly significant for all three traits evaluated and explained large proportion of the phenotypic variance for the three traits: 51.32% for AE, 55.93% for PP, and 48.48% for TS.

TABLE 3

QTL Mapping Results.

| Trait | QTL | Chr | Pos | Marker Interval | LOD | LOD(A) | LOD(AbyE) | PVE | PVE(A) | PVE(AbyE) | Add |
|---|---|---|---|---|---|---|---|---|---|---|---|
| AES | qAES1 | 1 | 168 | S1.199730599-S1.210741020 | 8.6 | 7.34 | 1.26 | 5.74 | 5.02 | 0.72 | −0.09 |
|  | qAES5 | 5 | 93 | S5.92720589-S5.92805032 | 59.81 | 44.56 | 15.25 | 51.33 | 35.91 | 15.42 | 0.44 |
|  | qAES6 | 6 | 82 | S6.111018551-S6.111368312 | 11.53 | 7.52 | 4.02 | 8 | 5.3 | 2.7 | 0.16 |
|  | qAES7 | 7 | 52 | S7.6435275-S7.10551600 | 6.18 | 4.38 | 1.8 | 3.95 | 3.05 | 0.9 | 0.02 |
|  | qAES10 | 10 | 94 | S10.133552715-S10.133703892 | 7.37 | 6.62 | 0.75 | 4.91 | 4.6 | 0.31 | −0.15 |
| PPS | qPPS1 | 1 | 168 | S1.199730599-S1.210741020 | 8.42 | 7.33 | 1.09 | 5.66 | 5.03 | 0.62 | −0.08 |
|  | qPPS5 | 5 | 93 | S5.92720589-S5.92805032 | 63.08 | 48.55 | 14.53 | 55.93 | 38.99 | 16.94 | 0.46 |
|  | qPPS6 | 6 | 82 | S6.111018551-S6.111368312 | 11.17 | 7.1 | 4.06 | 7.54 | 4.92 | 2.61 | 0.16 |
|  | qPPS7 | 7 | 52 | S7.6435275-S7.10551600 | 7.38 | 5.5 | 1.88 | 4.79 | 3.8 | 0.99 | 0.02 |
| TS | qTS5a | 5 | 93 | S5.92720589-S5.92805032 | 53.48 | 37.17 | 16.31 | 48.48 | 33.76 | 14.72 | 0.39 |
|  | qTS5b | 5 | 134 | S5.191768713-S5.191990245 | 6.32 | 4.03 | 2.3 | 4.86 | 3.19 | 1.67 | 0.1 |
|  | qTS6a | 6 | 82 | S6.111018551-S6.111368312 | 11.04 | 7.68 | 3.36 | 9.35 | 6.25 | 3.1 | 0.16 |
|  | qTS6b | 6 | 84 | S6.112600900-S6.112602435 | 8.14 | 2.21 | 5.93 | 6 | 1.79 | 4.21 | 0.09 |
|  | qTS7 | 7 | 52 | S7.6435275-S7.10551600 | 7.31 | 5.54 | 1.76 | 5.6 | 4.4 | 1.21 | 0.02 |
|  | qTS10 | 10 | 87 | S10.129355934-S10.130907871 | 6.31 | 3.74 | 2.56 | 4.98 | 3 | 1.98 | −0.1 |

Results

QTL Analysis for AE, PP, and TS Traits

A total of 21 QTL were detected for AE, PP, and TS in AEAE, AEAL, and PI. The detected QTL were found on a total five chromosomes. For the 21 QTL identified, 76% of loci had favorable alleles that originated from A427 and 24% of loci had favorable alleles that originated from CR1Ht. This indicates that both A427 and CR1Ht both carry favorable alleles for SHGD.

For AE, a total of 7 QTL were identified in three environments. The detected QTL were dispersed over chromosomes 1, 5, 6, 7, and 10. The phenotypic variance explained by additive effect QTLs was 3.51% to 42.19%. A major QTL, qAE5, was pinpointed to chromosome 5, was found in all 3 environments, and explained considerable percentage of phenotypic variation; 30.09% at PI, 41.58% at AEAL, and 42.19% at AEAE. The favorable allele came from inbred A427 for this region.

For PP, a total of 6 QTL were identified in three environments. The detected QTL were dispersed over chromosomes 1, 5, 6, and 7. The phenotypic variance explained by additive effect QTL was 3.51% to 41.80%. The same region on chromosome 5 identified for anther emergence was also determined to control pollen production, qPPS5. qPPS5 also Discussion The limiting factor in producing haploids is male fertility. Anther emergence, pollen production, and tassel size were used to assess SHGD. The objective of QTL mapping experiment was to identify genomic regions controlling spontaneous haploid genome doubling. The QTL analysis identified total of 21 QTL across three traits evaluated.

A novel large effect QTL with pleiotropy effects was found on chromosome 5. It showed pleiotropic effects for anther emergence, pollen production, and tassel size of the haploid and was found to be stable across all three environments that were tested. A minor effect QTL was also found with pleiotropic effects on chromosome 6. It shows pleiotropic effects for anther emergence, pollen production, and tassel size of the haploid as well, but only in a single environment, AF2.

For the MET analysis, a major QTL by environmental interaction was found for qTS6b. It was found that 70% of variation by the QTL that was control by additive by environment interaction. Across all traits, most didn't show an extreme QTL by environmental interaction. On average, the additive by environment interaction accounted for 30% of variation explained by QTL, where the other 70% of variation was additive. Since 30% of variation is not insignificant, environment does place a role in the expression of SHGD in field settings. Temperature and moisture could be affecting gene expression, which could be explaining the variation seen in this experiment.

Across all locations, 73% of GF1 haploids displayed anthers and pollen, 44% of GF3 haploids displayed anthers and pollen, and 32% of haploids from the mapping population displayed anthers and pollen. Since neither parent showed 100% fertility, a polygenic effect with multiple QTL is controlling SHGD. QTL were identified from both parents. This supports that different genetic backgrounds carry QTLs that contribute to SHGD. Screening material for SHGD maybe an effective strategy identifying new sources of SHGD. After the identification of the new sources of SHGD, the favorable QTL would pyramid together with the goal of improving SHGD.

This QTL study using GF1 as SHGD line and GF3 as parents, identified a single major QTL for PPS=(fertile) pollen production score on chromosome 5 near the centromere, where BUBR1 (GRMZM2G009913) is located. Chromosome 5 centromere is located from 101.6 Mb to 104.8 Mb based on ZmB73v1[8]. This QTL explains more than 50% of the phenotypic variation (PVE), more than the other detected QTL taken together. Thus, this gene can rather be considered as major gene, which simplifies incorporation into breeding populations (single versus multiple genes).

REFERENCES

1. Ren, J., Wu, P., Tian, X., Lübberstedt, T. & Chen, S. QTL mapping for haploid male fertility by a segregation distortion method and fine mapping of a key QTL qhmf4 in maize. *Theor Appl Genet* 130, 1349-1359 (2017).
2. Glaubitz, J. C. et al. TASSEL-GBS: A High Capacity Genotyping by Sequencing Analysis Pipeline. *PLOS ONE* 9, e90346 (2014).
3. Bradbury, P. J. et al. TASSEL: software for association mapping of complex traits in diverse samples. *Bioinformatics* 23, 2633-2635 (2007).
4. Miao, C. et al. Genotype-Corrector: improved genotype calls for genetic mapping in F2 and RIL populations. *Scientific Reports* 8, 10088 (2018).
5. Meng, L., Li, H., Zhang, L. & Wang, J. QTL IciMapping: Integrated software for genetic linkage map construction and quantitative trait locus mapping in biparental populations. *The Crop Journal* 3, 269-283 (2015).
6. Christensen, R. H. B. ordinal—Regression Models for Ordinal Data. (2018).
7. *R: A language and environment for statistical computing.* (R Foundation for Statistical Computing, 2018).
8. Wolfgruber, T. K. et al. Maize Centromere Structure and Evolution: Sequence Analysis of Centromeres 2 and 5 Reveals Dynamic Loci Shaped Primarily by Retrotransposons. *PLoS Genetics* 5, e1000743 (2009).

What is claimed is:

1. A method of breeding maize for spontaneous haploid genome doubling comprising:
   obtaining a source plant with a spontaneous haploid genome doubling locus comprising a variant BUBR1 gene;
   selecting said plant for use as a parent plant;
   crossing said parent plant with a second plant to produce a population of progeny plants; and
   genotyping one or more progeny plants with one or more nucleic acid markers within a chromosomal interval defined by and including the terminal markers 504_21 and umc2302 on maize chromosome 5 to determine if the progeny plant has the spontaneous haploid genome doubling locus.

2. The method of claim 1, wherein said source plant is A427.

3. A plant or plant part produced by the method of claim 1.

4. The method of claim 1, wherein the one or more nucleic acid markers comprise 504_21 and umc2302.

5. The method of claim 1, wherein the genotyping comprises detecting marker 504_21 with the primer pair of SEQ ID NO: 20 and 21.

6. The method of claim 1, wherein the genotyping comprises detecting marker umc2302 with the primer pair of SEQ ID NO: 22 and 23.

7. The method of claim 1, wherein the variant BUBR1 gene encodes a polypeptide having at least 95% sequence identity to SEQ ID NO: 3.

8. The method of claim 7, wherein the polypeptide comprises a valine at position 239 as set forth in SEQ ID NO: 3.

* * * * *